United States Patent
Edwards et al.

(10) Patent No.: US 9,675,567 B2
(45) Date of Patent: Jun. 13, 2017

(54) POTASSIUM ION CHANNEL MODULATORS AND USES THEREOF

(71) Applicant: Ramot at Tel-Aviv University Ltd., Tel-Aviv (IL)

(72) Inventors: Simon Edwards, Cambridge (GB); Ruth Meriel Kimberley, Cambridgeshire (GB); Richard Edward Armer, Cambridgeshire (GB); Mohammed Nawaz Khan, Cambridgeshire (GB)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/259,064

(22) Filed: Sep. 8, 2016

(65) Prior Publication Data

US 2016/0374969 A1 Dec. 29, 2016

Related U.S. Application Data

(62) Division of application No. 13/054,960, filed as application No. PCT/GB2009/050887 on Jul. 20, 2009, now Pat. No. 9,464,052.

(30) Foreign Application Priority Data

Jul. 22, 2008 (GB) .................................. 0813403.3

(51) Int. Cl.

| C07C 237/20 | (2006.01) |
|---|---|
| A61K 31/165 | (2006.01) |
| A61K 31/198 | (2006.01) |
| A61K 45/06 | (2006.01) |
| C07D 213/40 | (2006.01) |
| A61K 31/40 | (2006.01) |
| A61K 31/4402 | (2006.01) |
| A61K 31/445 | (2006.01) |
| A61K 31/5375 | (2006.01) |

(52) U.S. Cl.
CPC .......... *A61K 31/165* (2013.01); *A61K 31/198* (2013.01); *A61K 31/40* (2013.01); *A61K 31/4402* (2013.01); *A61K 31/445* (2013.01); *A61K 31/5375* (2013.01); *A61K 45/06* (2013.01); *C07C 237/20* (2013.01); *C07D 213/40* (2013.01)

(58) Field of Classification Search
CPC ..... A61K 31/165; A61K 31/198; A61K 46/06
See application file for complete search history.

(56) References Cited

U.S. PATENT DOCUMENTS

| 1,882,286 | A | 10/1932 | Laska et al. |
|---|---|---|---|
| 3,413,313 | A | 11/1968 | Scherrer |
| 4,181,519 | A | 1/1980 | Pilgram et al. |
| 5,347,036 | A | 9/1994 | Scherrer |
| 2005/0182040 | A1 | 8/2005 | Imazaki et al. |
| 2006/0270686 | A1 | 11/2006 | Kelly et al. |
| 2007/0072915 | A1 | 3/2007 | Lardy et al. |

FOREIGN PATENT DOCUMENTS

| CN | 101184726 | 5/2008 |
|---|---|---|
| DE | 1121925 | 1/1962 |
| EP | 1880720 | 1/2008 |
| JP | 53-092739 | 8/1978 |
| JP | 63-313765 | 12/1988 |
| JP | 03-278050 | 12/1991 |
| JP | 04-073190 | 3/1992 |
| JP | 08-501100 | 2/1996 |
| JP | 2001-526255 | 12/2001 |
| JP | 2003-527379 | 9/2003 |
| JP | 2006-513154 | 4/2006 |
| JP | 2006-526621 | 11/2006 |
| JP | 2008-524157 | 7/2008 |
| WO | WO 94/05153 | 3/1994 |
| WO | WO 99/32433 | 7/1999 |
| WO | WO 01/68619 | 9/2001 |
| WO | WO 03/076406 | 9/2003 |
| WO | WO 03/082808 | 10/2003 |
| WO | WO 2004/035037 | 4/2004 |
| WO | WO 2005/009344 | 2/2005 |
| WO | WO 2006/063999 | 6/2006 |
| WO | WO 2006/127133 | 11/2006 |
| WO | WO 2006/137376 | 12/2006 |
| WO | WO 2007/019914 | 2/2007 |
| WO | WO 2007/044565 | 4/2007 |

(Continued)

OTHER PUBLICATIONS

Communication Pursuant to Article 94(3) EPC Dated Nov. 5, 2015 From the European Patent Office Re. Application No. 09785362.6.
Communication Pursuant to Article 94(3) EPC Dated Dec. 17, 2013 From the European Patent Office Re. Application No. 09785362.6.
Examination Report Dated Mar. 25, 2015 From the Government of India, Patent Office, Intellectual Property Building Re. Application No. 251/MUMNP/2011.
International Preliminary Report on Patentability Dated Feb. 3, 2010 From the International Bureau of WIPO Re. Application No. PCT/GB2009/050887.
International Search Report and the Written Opinion Dated Nov. 26, 2009 From the International Searching Authority Re. Application No. PCT/GB2009/050887.
Notice of Reasons for Rejection Dated Oct. 29, 2013 From the Japanese Patent Office Re. Application No. 2011-519241 and Its Translation Into English.

(Continued)

*Primary Examiner* — Sahar Javanmard

(57) ABSTRACT

Compounds of formula (I):

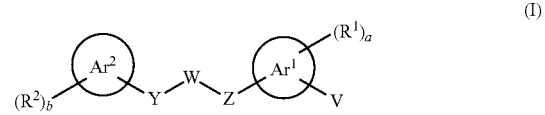

and pharmacologically acceptable salts and pro-drugs thereof, wherein the variables are as defined in the specification, are potassium ion channel modulators, making them particularly useful in treating and preventing conditions such as pain, lower urinary tract disorders and the like.

5 Claims, No Drawings

(56) References Cited

FOREIGN PATENT DOCUMENTS

WO    WO 2010/010380    1/2010

OTHER PUBLICATIONS

Office Action Dated Dec. 11, 2013 From the State Intellectual Property Office of the People's Republic of China Re. Application No. 200980137841.4 and Its Translation Into English.
Official Action Dated Aug. 13, 2015 From the US Patent and Trademark Office Re. U.S. Appl. No. 13/054,960.
Official Action Dated Dec. 16, 2013 From the US Patent and Trademark Office Re. U.S. Appl. No. 13/054,960.
Official Action Dated Jul. 31, 2014 From the US Patent and Trademark Office Re. U.S. Appl. No. 13/054,960.
Search Report Dated Dec. 11, 2013 From the State Intellectual Property Office of the People's Republic of China Re. Application No. 200980137841.4 and Its Translation Into English.
Translation of Office Action Dated Jan. 25, 2013 From the State Intellectual Property Office of the People's Republic of China Re. Application No. 200980137841.4.
Translation of Search Report Dated Jan. 25, 2013 From the State Intellectual Property Office of the People's Republic of China Re. Application No. 200980137841.4.
Chemical Abstracts "Glycine, N-(4-[(4-Methylphenyl)Amino]-3,5-Dinitrobenzoyl]", Database Registry [Online], Chemical Abstracts Service, Database Accession No. 613654-74-3, Nov. 7, 2003.
Corse et al. "Biosynthesis of Penicillins. V. Substituted Phenylacetic Acid Derivatives as Penicillin Precursors", Journal of the American Chemical Society, JACS, XP002235986, 70(9): 2837-2843, Sep. 30, 1948.
Huang et al. "Expanding Pd-Catalyzed C—N Bond-Forming Processes: The First Amidation of Aryl Sulfonates, Aqueous Amination, and Complementarity With Cu-Catalyzed Reactions", Journal of the American Chemical Society, JACS, XP002366815, 125(22): 6653-6655, Jan. 1, 2003. Expls.1, 3, Table 4.
Sorenson "Selective N-Arylation of Aminobenzanilides Under Mild Conditions Using Triarylbismuthanes", Journal of Organic Chemistry, 65: 7747-7749, 2000.
Ward et al. "Solid Phase Synthesis of Aryl Amines Via Palladium Catalyzed Amination of Resin-Bound Aromatic Bromides", Tetrahedron Letters, XP004030807, 37(39): 6993-6996, Sep. 23, 1996. Tables 1, 2.

POTASSIUM ION CHANNEL MODULATORS AND USES THEREOF

RELATED APPLICATIONS

This application is a division of U.S. patent application Ser. No. 13/054,960 filed on Jun. 20, 2011, which is a National Phase of PCT Patent Application No. PCT/GB2009/050887 having International Filing Date of Jul. 20, 2009, which claims the benefit of U.K. Patent Application No. 0813403.3 filed on Jul. 22, 2008. The contents of the above applications are all incorporated herein by reference.

FIELD AND BACKGROUND OF THE INVENTION

The present invention relates to ion channel modulators, and more particularly to heterocyclic compounds that modulate (preferably open) KCNQ2 (Kv7.2), KCNQ3 (Kv7.3) and KCNQ2/3 voltage-dependent potassium channels.

Voltage-dependent potassium (Kv) channels conduct potassium ions (K+) across cell membranes in response to change in the membrane voltage and thereby can regulate cellular excitability by modulating (increasing or decreasing) the electrical activity of the cell.

Functional Kv channels exist as multimeric structures formed by the association of four alpha and four beta subunits. The alpha subunits comprise six transmembrane domains, a pore-forming loop and a voltage-sensor and are arranged symmetrically around a central pore. The beta or auxiliary subunits interact with the alpha subunits and can modify the properties of the channel complex to include, but not be limited to, alterations in the channel's electrophysiological or biophysical properties, expression levels or expression patterns.

Functional Kv channels can exist as multimeric structures formed by the association of either identical or dissimilar Kv alpha and/or Kv beta subunits.

Nine Kv channel alpha subunit families have been identified and are termed Kv1-Kv9. As such, there is an enormous diversity in Kv channel function that arises as a consequence of the multiplicity of sub-families, the formation of both homomeric and heteromeric subunits within sub-families and the additional effects of association with beta subunits (M. J. Christie, Clinical and Experimental Pharmacology and Physiology, 1995, 22 (12), 944-951).

The Kv7 channel family consists of at least five members which include one or more of the following mammalian channels: Kv7.1, Kv7.2, Kv7.3, Kv7.4, Kv7.5 and any mammalian or non-mammalian equivalent or variant (including splice variants) thereof. Alternatively, the members of this family are termed KCNQ1, KCNQ2, KCNQ3, KCNQ4 and KCNQ5 respectively (Dalby-Brown. W et al., Current Topics in Medicinal Chemistry, 2006, 6, 999-1023).

The five members of this family differ in their expression patterns. The expression of Kv7.1 is restricted to the heart, peripheral epithelial and smooth muscle, whereas the expression of Kv7.2-Kv7.4 is limited to the nervous system to include the hippocampus, cortical neurons and dorsal root ganglion neurons (for a review see Delmas. P & Brown. D, Nature, 2005, 6, 850-862).

The neuronal Kv7 channels have been demonstrated to play key roles in controlling neuronal excitation. Kv7 channels, in particular Kv7.2/Kv7.3 heterodimers, underlie the M-current, a non-activating potassium current found in a number of neuronal cell types. The current has a characteristic time and voltage dependence that results in stabilisation of the membrane potential in response to multiple excitatory stimuli. In this way, the M-current is central to controlling neuronal excitability (for a review see Delmas. P & Brown. D, Nature, 2005, 6, 850-862).

The Kv7 channels are also clinically valuable targets, since mutations in the genes of four out of the five members gives rise to a number of human disorders. For example, mutations in the genes for KCNQ2 or KCNQ3 result in a form of juvenile epilepsy called benign familial neonatal convulsions (BNFC) (Jentsch, T. J., Nature Reviews Neuroscience, 2000, 1 (1), 21-30).

Thus, given the key physiological role of Kv7 channels in the nervous system and the involvement of these channels in a number of diseases, the development of modulators of Kv7 channels is very desirable.

Modulators of KCNQ2, KCNQ3 or KCNQ2/3 have potential utility in the treatment, prevention, inhibition, amelioration or alleviation of symptoms of a number of conditions or disease states including:

"Lower Urinary Tract Disorders", this encompasses both painful (any lower urinary tract disorder involving sensations or symptoms that a patient subjectively describes as producing or resulting in pain) and non-painful lower urinary tract disorders (any lower urinary tract disorder involving sensations or symptoms, including mild or general discomfort, that is subjectively described as not producing or resulting in pain). "Lower urinary tract disorders" also includes any lower urinary tract disorder characterised by overactive bladder with and/or without loss of urine, urinary frequency, urinary urgency, and nocturia. Thus, lower urinary tract disorders includes overactive bladder or overactive urinary bladder (including, overactive detrusor, detrusor instability, detrusor hyperreflexia, sensory urgency and the symptoms of detrusor overactivity), urge incontinence or urinary urge incontinence, stress incontinence or urinary stress incontinence, lower urinary tract symptoms including obstructive urinary symptoms such as slow urination, dribbling at the end of urination, inability to urinate and/or the need to strain to urinate at an acceptable rate or irritating symptoms such as frequency and/or urgency. Lower urinary tract disorders may also include neurogenic bladder that occurs as the result of neurological damage due to disorders including but not limited to stroke, Parkinson's disease, diabetes, multiple sclerosis, peripheral neuropathy, or spinal cord lesions. Lower urinary tract disorders may also include prostatitis, interstitial cystitis, benign prostatic hyperplasia, and, in spinal cord injured patients, spastic bladder.

"Anxiety and Anxiety-Related Conditions", this includes, but is not limited to, anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias. Specific anxiety related phobias include, but are not limited to, fear of animals, insects, storms, driving, flying, heights or crossing bridges, closed or narrow spaces, water; blood or injury, as well as extreme fear of inoculations or other invasive medical or dental procedures.

"Epilepsy", includes, but is not limited to, one or more of the following seizures: simple partial seizures, complex partial seizures, secondary generalised seizures, generalised seizures including absence seizures, myoclonic seizures, clonic seizures, tonic seizures, tonic clonic seizures and atonic seizures.

"Pain Disorders", includes but is not limited to one or more on the following: acute pain such as musculoskeletal pain, post-operative pain and surgical pain; chronic pain such as chronic inflammatory pain (e.g. rheumatoid arthritis and osteoarthritis), neuropathic pain (e.g. post-herpetic neuralgia, trigeminal neuralgia and sympathetically-maintained pain) and pain associated with cancer and fibromyalgia; pain associated with migraine; pain (both chronic and acute), and/or fever and/or inflammation of conditions such as rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin-related conditions, such as psoriasis, eczema, burns and dermatitis; injuries, such as sports injuries and those arising from surgical and dental procedures.

"Gynaecological Pain", for example, dysmenorrhoea, labour pain and pain associated with endometriosis.

"Cardiac Arrhythmias", include, but are not limited to, atrial fibrillation, atrial flutter, atrial arrhythmia and supaventricular tachycardia.

"Thromboembolic Events" such as stroke.

"Cardiovascular Diseases" such as angina pectoris, hypertension and congestive heart failure.

"Disorders of the Auditory System" such as tinnitus.

"Migraine"

"Inflammatory and Immunological Diseases" (or a disorder involving immunosuppression) including inflammatory bowel disease, rheumatoid arthritis, graft rejection, asthma, chronic obstructive pulmonary disease, multiple sclerosis, cystic fibrosis and atherosclerosis.

"Gastrointestinal Disorders" including reflux oesophagitis, functional dyspepsia, motility disorders (including constipation and diarrhoea), and irritable bowel syndrome.

"Vascular and Visceral Smooth Muscle Disorders" including asthma, pulmonary hypertension, chronic obstructive pulmonary disease, adult respiratory distress syndrome, peripheral vascular disease (including intermittent claudication), venous insufficiency, impotence, cerebral and coronary spasm and Raynaud's disease.

"Cell Proliferative Disorders" including restenosis and cancer (including leukemia); treating or preventing gliomas including those of lower and higher malignancy.

"Metabolic Disorders" such as diabetes (including diabetic retinopathy, diabetic nephropathy and diabetic neuropathy), insulin resistance/insensitivity and obesity.

"Memory Loss" including Alzheimer's disease and dementia.

Other "CNS-Mediated Motor Dysfunction Disorders" including Parkinson's disease and ataxia.

"Ophthalmic Disorders" such as ocular hypertension.

Retigabine is an anti-epileptic drug whose mechanism of action involves potassium channel opening activity in neuronal cells (first described in European Patent No. 0554543). Retigabine enhances potassium currents through specific activation of KCNQ2/3 channels (Wickenden, A. D., Molecular Pharmacology, 2000, 58, 591-600). However, retigabine has been reported to have multiple effects in neuronal cells. These include sodium and calcium channel blocking activity (Rundfeldt, C, 1995, Naunyn-Schmiederberg's Arch Pharmacol, 351 (Suppl): R160) and effects on GABA (γ-aminobutyric acid) synthesis and transmission in rat neurons (Kapetanovic, I. M., 1995, Epilepsy Research, 22, 167-173, Rundfeldt, C, 1995, Naunyn-Schmiederberg's Arch Pharmacol, 351 (Suppl):R160).

Thus, in order to overcome unwanted side effects, more selective Kv7 channel modulators are required.

WO04035037 discloses the use of N-phenylanthranilic acid derivatives as modulators of KCNQ2, KCNQ3 and KCNQ2/3 channels. These derivatives have substituents comprising hydroxyalkyl or polyalkylene glycol moieties that are linked to one of the phenyl groups of the N-phenylanthranilic acid moiety via a variety of linkers. The compounds disclosed therein all require the (CR3aR3b)pCON(R3b)X or (CR3aR3b)pN(R3b)CO(X) substituents on one of the aryl or heteroaryl groups to be ortho to the group linking said aryl or heteroaryl group to the other aryl or heteroaryl group.

It would be desirable to identify more selective Kv7 channel modulators for the prophylaxis or treatment of a number of disease states including lower urinary tract disorders, inflammatory and immunological diseases and pain indications. Using potassium ion channel patch clamp assays on KCNQ2, KCNQ3 and KCNQ2/3 channels recombinantly expressed in cells lines, a new family of N-phenylanthranilic acid compounds has been found that are excellent selective modulators of potassium ion flux through KCNQ2, KCNQ3 and/or KCNQ2/3 channels.

DESCRIPTION OF THE INVENTION

In a first aspect of the present invention, there is provided a compound of formula (I) or a pharmacologically acceptable salt or pro-drug thereof wherein:

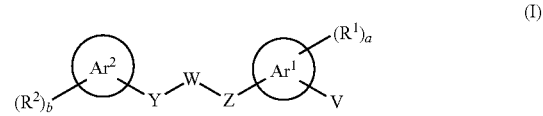

$Ar^1$ and $Ar^2$ are the same or different and each is an aryl group or a heteroaryl group;

a is an integer of from 0 to 5;

$R^1$ is selected from the group consisting of alkyl groups, halogen atoms, haloalkyl groups, alkoxy groups, haloalkoxy groups, alkoxycarbonyl groups, carboxyl groups, hydroxyl groups, amino groups, monoalkylamino groups, dialkylamino groups, nitro groups, acylamino groups, alkoxycarbonylamino groups, alkylsulphonyl groups, alkylsulphonylamino groups and cyano groups and, where a is greater than 1, each substituent $R^1$ may be the same or different; b is an integer of from 0 to 5;

$R^2$ is selected from the group consisting of alkyl groups, halogen atoms, haloalkyl groups, haloalkoxy groups, alkoxy groups, alkoxycarbonyl groups, carboxyl groups, hydroxyl groups, amino groups, monoalkylamino groups, dialkylamino groups, nitro groups, acylamino groups, alkoxycarbonylamino groups, alkylsulphonyl groups, alkylsulphonylamino groups and cyano groups and where b is greater than 1, each substituent $R^2$ may be the same or different;

V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z;

W is selected from the group consisting of $NR^{4a}$, O, S, S=O, $SO_2$ and $C(R^{4a}R^{4b})_2$;

X is a substituent selected from the group consisting of hydrogen atoms, alkyl groups, hydroxyalkyl groups, alkoxyalkyl groups, haloalkoxyalkyl groups, aryloxyalkyl groups, cycloalkyl groups, aryl groups, heteroaryl groups, polyalkylene glycol residues, aminoalkyl groups, monoalkylaminoalkyl groups, dialkylaminoalkyl groups; alkyl groups that are substituted with groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms (said saturated or partially unsaturated heterocyclic group optionally further being substituted by one or more substituents selected from the group consisting of alkyl groups, halogen atoms, haloalkyl groups, alkoxy groups, alkoxycarbonyl groups, carboxyl groups, nitro groups, amino groups, monoalkylamino groups, dialkylamino groups and hydroxyl groups), carboxyalkyl groups, alkoxycarbonylalkyl groups, haloalkoxycarbonylalkyl groups and aralkyloxycarbonylalkyl groups;

Y and Z are the same or different and each is a substituent selected from the group consisting of $(CR^{5a}R^{5b})_{n1}$, C=O, $SO_2$, $C(=O)NR^{5a}$, $C(=O)NR^{5a}SO_2$ and $C=O(R^{5a}R^{5b})_{n2}$;

$R^{3a}$, $R^{3b}$, $R^{4a}$, $R^{4b}$, $R^{5a}$ and $R^{5b}$ are the same or different and each is selected from the group consisting of hydrogen atoms, alkyl groups, cycloalkyl groups, aryl groups and heteroaryl groups;

n1 and n2 are the same or different and each is an integer of from 0 to 2; and p is an integer of from 0 to 2;

provided that:

(i) when $Ar^1$ is an aryl group, $Ar^2$ cannot be a group selected from thiazolyl, thiophenyl and pyridyl;

(ii) when $Ar^1$ and $Ar^2$ are both phenyl groups and the moiety —Y—W—Z— together represents —NH—CO—, V cannot represent a group of formula —CH(CH$_3$)—C(=O)NH$_2$; and (iii) when $Ar^1$ and $Ar^2$ are both phenyl groups and the moiety —Y—W—Z— together represents —NH—, V cannot represent a group of formula —CO—NH$_2$ or CO-Ph.

Preferred compounds of the present invention include:

(2) compounds according to (1) and pharmacologically acceptable salts and pro-drugs thereof, wherein $Ar^1$ and $Ar^2$ are the same or different and each is an aryl group having from 5 to 14 carbon atoms or a 5- to 7-membered aromatic heterocyclic group containing from 1 to 3 sulfur atoms, oxygen atoms and/or nitrogen atoms;

provided that:

(i) when $Ar^1$ is an aryl group, $Ar^2$ cannot be a group selected from thiazolyl, thiophenyl and pyridyl;

(ii) when $Ar^1$ and $Ar^2$ are both phenyl groups and the moiety —Y—W—Z— together represents —NH—CO—, V cannot represent a group of formula —CH(CH$_3$)—C(=O)NH$_2$; and (iii) when $Ar^1$ and $Ar^2$ are both phenyl groups and the moiety —Y—W—Z— together represents —NH—, V cannot represent a group of formula —CO—NH$_2$ or CO-Ph;

(3) compounds according to (1) and pharmacologically acceptable salts and pro-drugs thereof, wherein $Ar^1$ and $Ar^2$ are the same or different and each is an aryl group having from 6 to 10 carbon atoms or a 5- or 6-membered aromatic heterocyclic group containing 1 or 2 sulfur atoms, oxygen atoms and/or nitrogen atoms;

provided that:

(i) when $Ar^1$ is an aryl group, $Ar^2$ cannot be a group selected from thiazolyl, thiophenyl and pyridyl;

(ii) when $Ar^1$ and $Ar^2$ are both phenyl groups and the moiety —Y—W—Z— together represents —NH—CO—, V cannot represent a group of formula —CH(CH$_3$)—C(=O)NH$_2$; and (iii) when $Ar^1$ and $Ar^2$ are both phenyl groups and the moiety —Y—W—Z— together represents —NH—, V cannot represent a group of formula —CO—NH$_2$ or CO-Ph;

(4) compounds according to (1) and pharmacologically acceptable salts and pro-drugs thereof, wherein $Ar^1$ and $Ar^2$ are the same or different and each is selected from phenyl, pyridyl, furyl, thienyl and pyrrolyl groups;

provided that:

(i) when $Ar^1$ is a phenyl group, $Ar^2$ cannot be a pyridyl group;

(ii) when $Ar^1$ and $Ar^2$ are both phenyl groups and the moiety —Y—W—Z— together represents —NH—CO—, V cannot represent a group of formula —CH(CH$_3$)—C(=O)NH$_2$; and (iii) when $Ar^1$ and $Ar^2$ are both phenyl groups and the moiety —Y—W—Z— together represents —NH—, V cannot represent a group of formula —CO—NH$_2$ or CO-Ph;

(5) compounds according to (1) and pharmacologically acceptable salts and pro-drugs thereof, wherein $Ar^1$ and $Ar^2$ are each phenyl;

provided that:

(i) when the moiety —Y—W—Z— together represents —NH—CO—, V cannot represent a group of formula —CH(CH$_3$)—C(=O)NH$_2$; and (ii) when the moiety —Y—W—Z— together represents —NH—, V cannot represent a group of formula —CO—NH$_2$ or CO-Ph;

(6) compounds according to any one of (1) to (5) and pharmacologically acceptable salts and pro-drugs thereof, wherein a is an integer of from 0 to 3;

(7) compounds according to any one of (1) to (5) and pharmacologically acceptable salts and pro-drugs thereof, wherein a is 0 or 1;

(8) compounds according to any one of (1) to (7) and pharmacologically acceptable salts and pro-drugs thereof, wherein $R^1$ is selected from the group consisting of alkyl groups having from 1 to 6 carbon atoms, halogen atoms, haloalkyl groups having from 1 to 6 carbon atoms, haloalkoxy groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monoalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent $R^1$ may be the same or different;

(9) compounds according to any one of (1) to (7) and pharmacologically acceptable salts and pro-drugs thereof, wherein $R^1$ is selected from the group consisting of alkyl groups having from 1 to 4 carbon atoms, halogen atoms, haloalkyl groups having from 1 to 4 carbon atoms, haloalkoxy groups having from 1 to 4 carbon atoms, alkoxy groups having from 1 to 4 carbon atoms, carboxyl groups, hydroxyl groups, amino groups, monoalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

(10) compounds according to any one of (1) to (9) and pharmacologically acceptable salts and pro-drugs thereof, wherein b is an integer of from 0 to 4;

(11) compounds according to any one of (1) to (9) and pharmacologically acceptable salts and pro-drugs thereof, wherein b is an integer of from 0 to 3;

(12) compounds according to any one of (1) to (11) and pharmacologically acceptable salts and pro-drugs thereof, wherein $R^2$ is selected from the group consisting of alkyl groups having from 1 to 6 carbon atoms, halogen atoms, haloalkyl groups having from 1 to 6 carbon atoms, haloalkoxy groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monoalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent $R^2$ may be the same or different;

(13) compounds according to any one of (1) to (11) and pharmacologically acceptable salts and pro-drugs thereof, wherein $R^2$ is selected from the group consisting of alkyl groups having from 1 to 4 carbon atoms, halogen atoms, haloalkyl groups having from 1 to 4 carbon atoms, haloalkoxy groups having from 1 to 4 carbon atoms, alkoxy groups having from 1 to 4 carbon atoms, carboxyl groups, hydroxyl groups, amino groups, monoalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where b is greater than 1, each substituent $R^2$ may be the same or different;

(14) compounds according to any one of (1) to (11) and pharmacologically acceptable salts and pro-drugs thereof, wherein $R^2$ is selected from the group consisting of alkyl groups having from 1 to 3 carbon atoms, halogen atoms, haloalkyl groups having from 1 to 3 carbon atoms, haloalkoxy groups having from 1 to 3 carbon atoms, alkoxy groups having from 1 to 3 carbon atoms, carboxyl groups, amino groups, hydroxyl groups and cyano groups;

(15) compounds according to any one of (1) to (14) and pharmacologically acceptable salts and pro-drugs thereof, wherein W is selected from the group consisting of $NR^{4a}$, O, S, S=O, $SO_2$ and $C(R^{4a}R^{4b})_2$, wherein $R^{4a}$ and $R^{4b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms;

(16) compounds according to any one of (1) to (14) and pharmacologically acceptable salts and pro-drugs thereof, wherein W is selected from the group consisting of $NR^{4a}$, O and S, wherein $R^{4a}$ is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

(17) compounds according to any one of (1) to (14) and pharmacologically acceptable salts and pro-drugs thereof, wherein W is a group of formula $NR^{4a}$, wherein $R^{4a}$ is selected from the group consisting of hydrogen atoms, alkyl groups having from 1 to 3 carbon atoms and phenyl groups;

(18) compounds according to any one of (1) to (17) and pharmacologically acceptable salts and pro-drugs thereof, wherein Y and Z are the same or different and each is a substituent selected from the group consisting of $(CR^{5a}R^{5b})_{n1}$, C=O, $SO_2$, $C(=O)NR^{5a}$; $C(=O)NR^{5a}SO_2$ and $C=O(R_{5a}R_{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms;

(19) compounds according to any one of (1) to (17) and pharmacologically acceptable salts and pro-drugs thereof, wherein Y and Z are the same or different and each is a substituent selected from the group consisting of $(CR^{5a}R^{5b})_{n1}$, C=O and $C=O(R^{5a}R^{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

(20) compounds according to any one of (1) to (17) and pharmacologically acceptable salts and pro-drugs thereof, wherein Y and Z are each a group of formula $(CR^{5a}R^{5b})_{n1}$ wherein each n1 is 0;

(21) compounds according to any one of (1) to (20) and pharmacologically acceptable salts and pro-drugs thereof, wherein V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms, and X is a substituent selected from the group consisting of hydrogen atoms, alkyl groups having from 1 to 6 carbon atoms, hydroxyalkyl groups having from 1 to 6 carbon atoms, alkoxyalkyl groups comprising alkyl groups having from 1 to 6 carbon atoms which are substituted by at least one alkoxy group having from 1 to 6 carbon atoms, haloalkoxyalkyl groups comprising alkyl groups having from 1 to 6 carbon atoms which are substituted by at least one haloalkoxy group having from 1 to 6 carbon atoms, aryloxy groups having from 5 to 14 carbon atoms, cycloalkyl groups having from 3 to 7 carbon atoms, aryl groups having from 5 to 14 carbon atoms, 5- to 7-membered aromatic heterocyclic groups containing from 1 to 3 sulfur atoms, oxygen atoms and/or nitrogen atoms, polyalkylene glycol residues of general formula HO—[$(CR^{6a}R^{6b})_{c1}$—O—$(CR^{6c}R^{6d})_{c2}]_{c3}$— wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different from each other and each is a hydrogen atom or an alkyl group having from 1 to 6 carbon atoms, aminoalkyl groups having from 1 to 6 carbon atoms, monoalkylaminoalkyl groups comprising an aminoalkyl group having from 1 to 6 carbon atoms that is substituted on the nitrogen atom with an alkyl group having from 1 to 6 carbon atoms, dialkylaminoalkyl groups comprising an aminoalkyl group having from 1 to 6 carbon atoms that is substituted on the nitrogen atom with two alkyl groups that may be the same or different and each is an alkyl group having from 1 to 6 carbon atoms, alkyl groups that are substituted with groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms comprising an alkyl group having form 1 to 6 carbon atoms that is substituted with a group of formula NR8R9 wherein R8 and R9 together with the nitrogen atom to which they are attached form a 4- to 14-membered nitrogen-containing saturated or partially unsaturated heterocyclic group having one or more rings (including bridged saturated or partially unsaturated heterocyclic groups having one or more rings), which optionally further contains one or more additional nitrogen, oxygen or sulphur atoms (wherein said saturated or partially unsaturated heterocyclic group is optionally substituted by one or more substituents selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups comprising carbonyl groups that are substituted by alkoxy groups having from 1 to 6 carbon atoms, carboxyl groups, nitro groups, amino groups, monoalkylamino groups wherein the alkyl groups have from 1 to 6 carbon atoms, dialkylamino groups wherein each alkyl group is the same or different and each is an alkyl group having from 1 to 6 carbon atoms and hydroxyl groups), carboxyalkyl groups comprising alkyl groups having from 1 to 6 carbon atoms which are substituted with at least one carboxy group, alkoxycarbonylalkyl groups comprising alkyl groups having from 1 to 6 carbon atoms which are substituted with at least one alkoxycarbonyl group having from 2 to 7 carbon atoms, haloalkoxycarbonylalkyl groups comprising carbonylalkyl groups having from 2 to 7 carbon atoms that are substituted eith haloalkoxy groups having from 1 to 6 carbon atoms and aralkyloxycarbonylalkyl groups comprising carbonylalkyl groups having from 2 to 7 carbon atoms which are substituted with at least one aralkyloxy group that comprises an alkyl group having from 1 to 6 carbon atoms that is substituted with an aryl group having from 5 to 14 carbon atoms;

(22) compounds according to any one of (1) to (20) and pharmacologically acceptable salts and pro-drugs thereof, wherein V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z, wherein p is an integer of 0 or 1, $R^{3a}$ and $R^{3b}$ are the same or different and each is selected from the group consisting of hydrogen atoms and alkyl groups having from 1 to 4 carbon atoms, and X is a substituent selected from the group consisting of hydrogen atoms, alkyl groups having from 1 to 4 carbon atoms, hydroxyalkyl groups having from 1 to 4 carbon atoms, polyalkylene glycol residues of general formula HO—[$(CR^{6a}R^{6b})_{c1}$—O—$(CR^{6c}R^{6d})_{c2}]_{c3}$— wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different and each is a hydrogen atom or an alkyl group having from 1 to 4 carbon atoms, alkoxyalkyl groups comprising an alkyl group having from 1 to 4 carbon atoms that is substituted with at least one alkoxy group having from 1 to 4 carbon atoms, carboxyalkyl groups comprising an alkyl group having from 1 to 4 carbon atoms that is substituted with at least one carboxy group, aminoalkyl groups having from 1 to 4 carbon atoms, monoalkylaminoalkyl groups comprising an aminoalkyl group having from 1 to 4 carbon atoms wherein the amino group is substituted with an alkyl group having from 1 to 4 carbon atoms, dialkylaminoalkyl groups comprising an aminoalkyl group having from 1 to 4 carbon atoms wherein the amino group is substituted with two alkyl groups having from 1 to 4 carbon atoms that may be the same or different, an alkyl group having from 1 to 4 carbon atoms that is substituted with a group of formula NR8R9 wherein R8 and R9 together with the nitrogen atom to which it is attached forms a 4- to 8-membered saturated or partially unsaturated nitrogen-containing heterocyclic group having one or more rings (including bridged saturated or partially unsaturated heterocyclic groups having one or more rings), which optionally further contains one or more additional nitrogen, oxygen or sulphur atoms (wherein said saturated or partially unsaturated heterocyclic group is optionally substituted by one or more substituents selected from the group consisting of alkyl groups having from 1 to 4 carbon atoms, halogen atoms, haloalkyl groups having from 1 to 4 carbon atoms, alkoxy groups having from 1 to 4 carbon atoms, alkoxycarbonyl groups comprising carbonyl groups that are substituted by alkoxy groups having from 1 to 4 carbon atoms, carboxyl groups, nitro groups, amino groups, monoalkylamino groups wherein the alkyl groups have from 1 to 4 carbon atoms, dialkylamino groups wherein each alkyl group is the same or different and each is an alkyl group having from 1 to 4 carbon atoms and hydroxyl groups), carboxyalkyl groups comprising alkyl groups having from 1 to 4 carbon atoms which are substituted with at least one carboxy group and alkoxycarbonylalkyl groups comprising alkyl groups having from 1 to 4 carbon atoms which are substituted with at least one alkoxycarbonyl group having from 2 to 5 carbon atoms;

(23) compounds according to any one of (1) to (20) and pharmacologically acceptable salts and pro-drugs thereof, wherein V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z, wherein p is an integer of 0 or 1, each of $R^{1a}$ and $R^{1b}$ is a hydrogen atom, and X is selected from the group consisting of alkyl groups having 1 or 2 carbon atoms which are substituted with a group selected from hydroxyl groups, methoxy groups, ethoxy groups, carboxy groups, methoxycarbonyl groups, ethoxycarbonyl, groups, methoxy groups, ethoxy groups, amino groups, methylamino groups, dimethylamino groups, diethylamino groups, piperazin-1-yl groups, 4-methylpiperazin-1-yl groups, morpholin-4-yl, 3-hydroxy-pyrrolidin-1-yl, 4,4-difluoro-piperidin-1-yl, pyridin-2-yl and 4-methoxycarbonylpiperazin-1-yl groups;

(24) a compound according to (1) or a pharmacologically acceptable salt or pro-drug thereof, wherein:

$Ar^1$ and $Ar^2$ are the same or different and each is an aryl group having from 5 to 14 carbon atoms or a 5- to 7-membered aromatic heterocyclic group containing from 1 to 3 sulfur atoms, oxygen atoms and/or nitrogen atoms;

a is an integer of from 0 to 3;

$R^1$ is selected from the group consisting of alkyl groups having from 1 to 6 carbon atoms, halogen atoms, haloalkyl groups having from 1 to 6 carbon atoms, alkoxy groups having from 1 to 6 carbon atoms, haloalkoxy groups having from 1 to 6 carbon atoms, alkoxycarbonyl groups wherein the alkoxy group has from 1 to 6 carbon atoms, carboxyl groups, hydroxyl groups, amino groups, monoalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent may be the same or different;

b is an integer of from 0 to 4;

$R^2$ is selected from the group consisting of alkyl groups having from 1 to 6 carbon atoms, halogen atoms, haloalkyl groups having from 1 to 6 carbon atoms, alkoxy groups having from 1 to 6 carbon atoms, haloalkoxy groups having from 1 to 6 carbon atoms, alkoxycarbonyl groups wherein the alkoxy group has from 1 to 6 carbon atoms, carboxyl groups, hydroxyl groups, amino groups, monoalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent $R^2$ may be the same or different;

W is selected from the group consisting of $NR^{4a}$, O, S, S=O, $SO_2$ or $C(R^{4a}R^{4b})_2$, wherein $R^{4a}$ and $R^{4b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms; Y and Z are the same or different and each is a substituent selected from the group consisting of $(CR^{5a}R^{5b})_{n1}$, C=O, $SO_2$, C(=O)$NR^{5a}$; C(=O)$NR^{5a}SO_2$ and C=O$(R^{5a}R^{5b})_2$, wherein n1 and n2 are the same or different and each is 0 or 1 and $R^{5a}$ and $R^{5b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms; and V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms, and X is a substituent selected from the group consisting of hydrogen atoms, alkyl groups having from 1 to 6 carbon atoms, hydroxyalkyl groups having from 1 to 6 carbon atoms, alkoxyalkyl groups comprising alkyl groups having from 1 to 6 carbon atoms which are substituted by at least one alkoxy group having from 1 to 6 carbon atoms, haloalkoxyalkyl groups comprising alkyl groups having from 1 to 6 carbon atoms which are substituted by at least one haloalkoxy group having from 1 to 6 carbon atoms, aryloxy groups having from 5 to 14 carbon atoms, cycloalkyl groups having from 3 to 7 carbon atoms, aryl groups having from 5 to 14 carbon atoms, 5- to 7-membered aromatic heterocyclic groups containing from 1 to 3 sulfur atoms, oxygen atoms and/or nitrogen atoms, polyalkylene glycol residues of general formula HO—$[(CR^{6a}R^{6b})_{c1}$—O—$(CR^{6c}R^{6d})_{c2}]_{c3}$— wherein c1 and c2 are the same or different and each is an integer of from 0 to 4, c3 is an integer of from 1 to 20 and $R^{ha}$, $R^{6b}$, $R^{ho}$ and $R^{6d}$ may be the same or different from each other and each is a hydrogen atom or an alkyl group having from 1 to 6 carbon atoms, aminoalkyl groups having from 1 to 6 carbon atoms, monoalkylaminoalkyl groups comprising an aminoalkyl group having from 1 to 6 carbon atoms that is substituted on the nitrogen atom with an alkyl group having from 1 to 6 carbon atoms, dialkylaminoalkyl groups comprising an aminoalkyl group having from 1 to 6 carbon atoms that is substituted on the nitrogen atom with two alkyl groups that may be the same or different and each is an alkyl group having from 1 to 6 carbon atoms, alkyl groups that are substituted with groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms comprising an alkyl group having form 1 to 6 carbon atoms that is substituted with a group of formula NR8R9 wherein R8 and R9 together with the nitrogen atom to which they are attached form a 4- to 14-membered nitrogen-containing saturated or partially unsaturated heterocyclic group having one or more rings (including bridged saturated or partially unsaturated heterocyclic groups having one or more rings), which optionally further contains one or more additional nitrogen, oxygen or sulphur atoms (wherein said saturated or partially unsaturated heterocyclic group is optionally substituted by one or more substituents selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups comprising carbonyl groups that are substituted by alkoxy groups having from 1 to 6 carbon atoms, carboxyl groups, nitro groups, amino groups, monoalkylamino groups wherein the alkyl groups have from 1 to 6 carbon atoms, dialkylamino groups wherein each alkyl group is the same or different and each is an alkyl group having from 1 to 6 carbon atoms and hydroxyl groups), carboxyalkyl groups comprising alkyl groups having from 1 to 6 carbon atoms which are substituted with at least one carboxy group, alkoxycarbonylalkyl groups comprising alkyl groups having from 1 to 6 carbon atoms which are substituted with at least one alkoxycarbonyl group having from 2 to 7 carbon atoms, haloalkoxycarbonylalkyl groups comprising carbonylalkyl groups having from 2 to 7 carbon atoms that are substituted eith haloalkoxy groups having from 1 to 6 carbon atoms and aralkyloxycarbonylalkyl groups comprising carbonylalkyl groups having from 2 to 7 carbon atoms which are substituted with at least one aralkyloxy group that comprises an alkyl group having from 1 to 6 carbon atoms that is substituted with an aryl group having from 5 to 14 carbon atoms;

provided that:

(i) when $Ar^1$ is an aryl group, $Ar^2$ cannot be a group selected from thiazolyl, thiophenyl and pyridyl;

(ii) when $Ar^1$ and $Ar^2$ are both phenyl groups and the moiety —Y—W—Z— together represents —NH—CO—, V cannot represent a group of formula —CH(CH$_3$)—C(=O)NH$_2$; and (iii) when $Ar^1$ and $Ar^2$ are both phenyl groups and the moiety —Y—W—Z— together represents —NH—, V cannot represent a group of formula —CO—NH$_2$ or CO-Ph;

(25) a compound according to (1) or a pharmacologically acceptable salt or pro-drug thereof, wherein:

$Ar^1$ and $Ar^2$ are the same or different and each is an aryl group having from 6 to 10 carbon atoms or a 5- or 6-membered aromatic heterocyclic group containing 1 or 2 sulfur atoms, oxygen atoms and/or nitrogen atoms;

a is 0 or 1;

$R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, haloalkoxy groups having from 1 to 4 carbon atoms, carboxyl groups, hydroxyl groups, amino groups, monoalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

b is an integer of from 0 to 3;

$R^2$ is selected from the group consisting of alkyl groups having from 1 to 4 carbon atoms, halogen atoms, haloalkyl groups having from 1 to 4 carbon atoms, alkoxy groups having from 1 to 4 carbon atoms, haloalkoxy groups having from 1 to 4 carbon atoms, carboxyl groups, hydroxyl groups, amino groups, monoalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where b is greater than 1, each substituent $R^2$ may be the same or different;

W is selected from the group consisting of $NR^{4a}$, O or S, wherein $R^{4a}$ is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

Y and Z are the same or different and each is a substituent selected from the group consisting of $(CR^{5a}R^{5b})_{n1}$, C=O and C=O($R^{5a}R^{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms; and V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z, wherein p is an integer of 0 or 1, $R^{3a}$ and $R^{3b}$ are the same or different and each is selected from the group consisting of hydrogen atoms and alkyl groups having from 1 to 4 carbon atoms, and X is a substituent selected from the group consisting of hydrogen atoms, alkyl groups having from 1 to 4 carbon atoms, hydroxyalkyl groups having from 1 to 4 carbon atoms, polyalkylene glycol residues of general formula HO—[(CR$^{6a}$R$^{6b}$)$_{c1}$—O—(CR$^{6c}$R$^{6c}$)$_{c2}$]$_{c2}$— wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different and each is a hydrogen atom or an alkyl group having from 1 to 4 carbon atoms, alkoxyalkyl groups comprising an alkyl group having from 1 to 4 carbon atoms that is substituted with at least one alkoxy group having from 1 to 4 carbon atoms, carboxyalkyl groups comprising an alkyl group having from 1 to 4 carbon atoms that is substituted with at least one carboxy group, aminoalkyl groups having from 1 to 4 carbon atoms, monoalkylaminoalkyl groups comprising an aminoalkyl group having from 1 to 4 carbon atoms wherein the amino group is substituted with an alkyl group having from 1 to 4 carbon atoms, dialkylaminoalkyl groups comprising an aminoalkyl group having from 1 to 4 carbon atoms wherein the amino group is substituted with two alkyl groups having from 1 to 4 carbon atoms that may be the same or different, an alkyl group having from 1 to 4 carbon atoms that is substituted with a group of formula NR8R9 wherein R8 and R9 together with the nitrogen atom to which it is attached forms a 4- to 8-membered saturated or partially unsaturated nitrogen-containing heterocyclic group having one or more rings (including bridged saturated or partially unsaturated heterocyclic groups having one or more rings), which optionally further contains one or more additional nitrogen, oxygen or sulphur atoms (wherein said saturated or partially unsaturated heterocyclic group is optionally substituted by one or more substituents selected from the group consisting of alkyl groups having from 1 to 4 carbon atoms, halogen atoms, haloalkyl groups having from 1 to 4 carbon atoms, alkoxy groups having from 1 to 4 carbon atoms, alkoxycarbonyl groups comprising carbonyl groups that are substituted by alkoxy groups having from 1 to 4 carbon atoms, carboxyl groups, nitro groups, amino groups, monoalkylamino groups wherein the alkyl groups have from 1 to 4 carbon atoms, dialkylamino groups wherein each alkyl group is the same or different and each is an alkyl group having from 1 to 4 carbon atoms and hydroxyl groups), carboxyalkyl groups comprising alkyl groups having from 1 to 4 carbon atoms which are substituted with at least one carboxy group and alkoxycarbonylalkyl groups comprising alkyl groups having from 1 to 4 carbon atoms which are substituted with at least one alkoxycarbonyl group having from 2 to 5 carbon atoms;

provided that:

(i) when $Ar^1$ is an aryl group, $Ar^2$ cannot be a group selected from thiazolyl, thiophenyl and pyridyl; and (ii) when $Ar^1$ and $Ar^2$ are both phenyl groups and the moiety —Y—W—Z— together represents —NH—, V cannot represent a group of formula —CO—NH$_2$ or CO-Ph;

(26) a compound according to (1) or a pharmacologically acceptable salt or pro-drug thereof, wherein:

$Ar^1$ and $Ar^2$ are each phenyl;

a is 0 or 1;

$R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, haloalkoxy groups having from 1 to 4 carbon atoms, carboxyl groups, hydroxyl groups, amino groups, monoalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

b is 0 to 3;

$R^2$ is selected from the group consisting of alkyl groups having from 1 to 3 carbon atoms, halogen atoms, haloalkyl groups having from 1 to 3 carbon atoms, alkoxy groups having from 1 to 3 carbon atoms, haloalkoxy groups having from 1 to 3 carbon atoms, carboxyl groups, amino groups, hydroxyl groups and cyano groups;

W is a group of formula $NR^{4a}$, wherein $R^{4a}$ is selected from the group consisting of hydrogen atoms, alkyl groups having from 1 to 3 carbon atoms and phenyl groups;

Y and Z are each a group of formula $(CR^{5a}R^{5b})_{n1}$ wherein each n1 is 0; and V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z, wherein p is an integer of 0 or 1, each of $R^{3a}$ and $R^{3b}$ is a hydrogen atom, and X is selected from the group consisting of alkyl groups having 1 or 2 carbon atoms which are substituted with a group selected from hydroxyl groups, methoxy groups, ethoxy groups, carboxy groups, methoxycarbonyl groups, ethoxycarbonyl, groups, methoxy groups, ethoxy groups, amino groups, methylamino groups, dimethylamino groups, diethylamino groups, piperazin-1-yl groups, 4-methylpiperazin-1-yl groups, morpholin-4-yl, 3-hydroxy-pyrrolidin-1-yl, 4,4-difluoro-piperidin-1-yl, pyridin-2-yl and 4-methoxycarbonylpiperazin-1-yl groups;

provided that:

(i) when $Ar^1$ and $Ar^2$ are both phenyl groups and the moiety —Y—W—Z— together represents —NH—, V cannot represent a group of formula —CO—NH$_2$ or CO-Ph; and

(27) A compound according to (1) or a pharmacologically acceptable salt or pro-drug thereof, selected from the group consisting of:

N-(2-hydroxyethyl)-2-[3-(2,4,6-trichlorophenylamino)phenyl]acetamide;

{2-[5-(3,5-dichlorophenylamino)-2-fluorophenyl]-acetylamino}acetic acid;

2-[4-(2,6-dichloro-4-trifluoromethyl-phenylamino)-phenyl]-N-(2-hydroxyethyl)-acetamide;

{2-[4-(3,5-dichlorophenylamino)-phenyl]-acetylamino}acetic acid;

N-(2-hydroxy-ethyl)-2-[4-(2,4,6-trichloro-phenylamino)-phenyl]acetamide;

3-(2,6-dichloro-4-trifluoromethyl-phenylamino)-N-(2-hydroxy-ethyl)benzamide;

2-[2-fluoro-5-(2,4,6-trichloro-phenylamino)-phenyl]-N-(2-hydroxy-ethyl)acetamide;

2-[5-(2,6-dichloro-4-trifluoromethyl-phenylamino)-2-fluoro-phenyl]-N-(2-morpholin-4-yl-ethyl)acetamide;

2-[2-fluoro-5-(2,4,6-trichloro-phenylamino)-phenyl]-N-(2-morpholin-4-yl-ethyl)-acetamide;

2-[5-(2,6-dichloro-4-trifluoromethyl-phenylamino)-2-fluoro-phenyl]-N-(2-hydroxy-ethyl)acetamide;

2-[5-(2,6-dichloro-4-trifluoromethoxy-phenylamino)-2-fluoro-phenyl]-N-(2-hydroxy-ethyl)acetamide;

2-[4-(2,6-dichloro-4-trifluoromethoxy-phenylamino)-phenyl]-N-(2-hydroxy-ethyl)-acetamide;

5-(2,6-dichloro-4-trifluoromethyl-phenylamino)-2-fluoro-N-(2-hydroxy-ethyl)-benzamide;

2-[4-(2,6-dichloro-4-trifluoromethyl-phenylamino)-phenyl]-N-(2-hydroxy-2-methyl-propyl)acetamide;

2-[5-(2,6-dichloro-4-trifluoromethyl-phenylamino)-2-fluoro-phenyl]-N-(2-hydroxy-2-methyl-propyl)acetamide;

2-[5-(2,6-dichloro-4-trifluoromethyl-phenylamino)-2-fluoro-phenyl]acetamide;

2-[5-(2,6-dichloro-4-trifluoromethyl-phenylamino)-2-fluoro-phenyl]-1-(3-hydroxy-pyrrolidin-1-yl)ethanone;

2-[4-(2,6-dichloro-4-trifluoromethoxy-phenylamino)-2-fluoro-phenyl]-N-(2-hydroxy-ethyl)propionamide;

2-[4-(2,6-dichloro-4-trifluoromethyl-phenylamino)-phenyl]-N-(2-morpholin-4-yl-ethyl)acetamide;

2-[5-(2,6-dichloro-4-trifluoromethyl-phenylamino)-2-fluoro-phenyl]-N-[2-(4,4-difluoropiperidin-1-yl)-ethyl]acetamide;

2-[5-(2,6-dichloro-4-trifluoromethyl-phenylamino)-2-fluoro-phenyl]-N-(2-pyridin-2-yl-ethyl)acetamide; and 2-[5-(2,6-dichloro-4-trifluoromethyl-phenylamino)-2-fluoro-phenyl]-N-pyridin-2-ylmethylacetamide.

In a second aspect of the present invention, there is provided a pharmaceutical composition comprising a pharmacologically acceptable diluent or carrier and an active ingredient, wherein said active ingredient is a compound according to any one of (1) to (27) or a pharmacologically acceptable salt or prodrug thereof as an active ingredient thereof.

In a third aspect of the present invention, there is provided a compound according to any one of (1) to (27) or a pharmacologically acceptable salt or prodrug thereof for use as a medicament.

In a fourth aspect of the present invention, there is provided use of a compound according to any one of (1) to (27) or a pharmacologically acceptable salt or prodrug thereof in the preparation of a medicament for the prophylaxis or treatment of a disease in which KCNQ2, KCNQ3 or KCNQ2/3 channels are involved.

In a fifth aspect of the present invention, there is provided use of a compound according to any one of (1) to (27) or a pharmacologically acceptable salt or prodrug thereof in the preparation of a medicament for the prophylaxis or treatment of a condition or disease ameliorated by KCNQ2, KCNQ3 or KCNQ2/3 channel opening.

In a sixth aspect of the present invention, there is provided use of a compound of formula (Ia) as defined below or a pharmaceutically acceptable salt or prodrug thereof in the preparation of a medicament for the prophylaxis or treatment of Lower Urinary Tract Disorders:

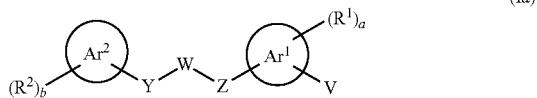

wherein:
Ar¹ and Ar² are the same or different and each is an aryl group or a heteroaryl group;
a is an integer of from 0 to 5;
R¹ is selected from the group consisting of alkyl groups, halogen atoms, haloalkyl groups, alkoxy groups, haloalkoxy groups, alkoxycarbonyl groups, carboxyl groups, hydroxyl groups, amino groups, monoalkylamino groups, dialkylamino groups, nitro groups, acylamino groups, alkoxycarbonylamino groups, alkylsulphonyl groups, alkylsulphonylamino groups and cyano groups and, where a is greater than 1, each substituent R¹ may be the same or different;
b is an integer of from 0 to 5;
R² is selected from the group consisting of alkyl groups, halogen atoms, haloalkyl groups, haloalkoxy groups, alkoxy groups, alkoxycarbonyl groups, carboxyl groups, hydroxyl groups, amino groups, monoalkylamino groups, dialkylamino groups, nitro groups, acylamino groups, alkoxycarbonylamino groups, alkylsulphonyl groups, alkylsulphonylamino groups and cyano groups and where b is greater than 1, each substituent R² may be the same or different;
V is selected from the group consisting of $(CR^{3a}R^{3b})_p CON(R^{3b})X$ and $(CR^{3a}R^{3b})_p N(R^{3b})CO(X)$, wherein said groups are in the 3-(meta) or 4-(para) position with respect to the substituent Z;
W is selected from the group consisting of $NR^{4a}$, O, S, S=O, $SO_2$ and $C(R^{4a}R^{4b})_2$;
X is a substituent selected from the group consisting of hydrogen atoms, alkyl groups, hydroxyalkyl groups, alkoxyalkyl groups, haloalkoxyalkyl groups, aryloxyalkyl groups, cycloalkyl groups, aryl groups, heteroaryl groups, polyalkylene glycol residues, aminoalkyl groups, monoalkylaminoalkyl groups, dialkylaminoalkyl groups; alkyl groups that are substituted with groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms (said saturated or partially unsaturated heterocyclic group optionally further being substituted by one or more substituents selected from the group consisting of alkyl groups, halogen atoms, haloalkyl groups, alkoxy groups, alkoxycarbonyl groups, carboxyl groups, nitro groups, amino groups, monoalkylamino groups, dialkylamino groups and hydroxyl groups), carboxyalkyl groups, alkoxycarbonylalkyl groups, haloalkoxycarbonylalkyl groups and aralkyloxycarbonylalkyl groups;
Y and Z are the same or different and each is a substituent selected from the group consisting of $(CR^{5a}R^{5b})_{n1}$, C=O, $SO_2$, $C(=O)NR^{5a}$; $C(=O)NR^{5a}SO_2$ and $C=O(R^{5a}R^{5b})_{n2}$;

$R^{3a}$, $R^{3b}$, $R^{4a}$, $R^{4b}$, $R^{5a}$ and $R^{5b}$ are the same or different and each is selected from the group consisting of hydrogen atoms, alkyl groups, cycloalkyl groups, aryl groups and heteroaryl groups;
n1 and n2 are the same or different and each is an integer of from 0 to 2; and
p is an integer of from 0 to 2.

In an seventh aspect of the present invention, there is provided use of a compound according to any one of (1) to (27) or a pharmacologically acceptable salt or prodrug thereof in the preparation of a medicament for the prophylaxis or treatment of Anxiety and Anxiety-Related Conditions.

In a eighth aspect of the present invention, there is provided use of a compound according to any one of (1) to (27) or a pharmacologically acceptable salt or prodrug thereof in the preparation of a medicament for the prophylaxis or treatment of Epilepsy.

In a ninth aspect of the present invention, there is provided use of a compound according to any one of (1) to (27) or a pharmacologically acceptable salt or prodrug thereof in the preparation of a medicament for the prophylaxis or treatment of Pain Disorders.

In a tenth aspect of the present invention, there is provided use of a compound of formula (Ia) as defined in the sixth aspect of the present invention or a pharmacologically acceptable salt or prodrug thereof in the preparation of a medicament for the prophylaxis or treatment of Gynaecological Pain.

In an eleventh aspect of the present invention, there is provided use of a compound of formula (Ia) as defined in the sixth aspect of the present invention or a pharmacologically acceptable salt or prodrug thereof in the preparation of a medicament for the prophylaxis or treatment of Cardiac Arrhythmias.

In a twelfth aspect of the present invention, there is provided use of a compound of formula (Ia) as defined in the sixth aspect of the present invention or a pharmacologically acceptable salt or prodrug thereof in the preparation of a medicament for the prophylaxis or treatment of Thromboembolic Events.

In a thirteenth aspect of the present invention, there is provided use of a compound of formula (Ia) as defined in the sixth aspect of the present invention or a pharmacologically acceptable salt or prodrug thereof in the preparation of a medicament for the prophylaxis or treatment of Cardiovascular Diseases.

In a fourteenth aspect of the present invention, there is provided use of a compound according to any one of (1) to (27) or a pharmacologically acceptable salt or prodrug thereof in the preparation of a medicament for the prophylaxis or treatment of Disorders of the Auditory System.

In a fifteenth aspect of the present invention, there is provided use of a compound according to any one of (1) to (27) or a pharmacologically acceptable salt or prodrug thereof in the preparation of a medicament for the prophylaxis or treatment of Migraine.

In a sixteenth aspect of the present invention, there is provided use of a compound according to any one of (1) to (27) or a pharmacologically acceptable salt or prodrug thereof in the preparation of a medicament for the prophylaxis or treatment of Inflammatory and Immunological Diseases.

In an seventeenth aspect of the present invention, there is provided use of a compound of formula (Ia) as defined in the sixth aspect of the present invention or a pharmacologically acceptable salt or prodrug thereof in the preparation of a medicament for the prophylaxis or treatment of Gastrointestinal Disorders.

In an eighteenth aspect of the present invention, there is provided use of a compound of formula (Ia) as defined in the sixth aspect of the present invention or a pharmacologically acceptable salt or prodrug thereof in the preparation of a medicament for the prophylaxis or treatment of Vascular and Visceral Smooth Muscle Disorders.

In a nineteenth aspect of the present invention, there is provided use of a compound according to any one of (1) to (27) or a pharmacologically acceptable salt or prodrug thereof in the preparation of a medicament for the prophylaxis or treatment of Cell Proliferative Disorders.

In a twentieth aspect of the present invention, there is provided use of a compound according to any one of (1) to (27) or a pharmacologically acceptable salt or prodrug thereof in the preparation of a medicament for the prophylaxis or treatment of Metabolic Disorders.

In a twenty-first aspect of the present invention, there is provided use of a compound according to any one of (1) to (27) or a pharmacologically acceptable salt or prodrug thereof in the preparation of a medicament for the prophylaxis or treatment of Memory Loss.

In a twenty-second aspect of the present invention, there is provided use of a compound according to any one of (1) to (27) or a pharmacologically acceptable salt or prodrug thereof in the preparation of a medicament for the prophylaxis or treatment of CNS-Mediated Motor Dysfunction Disorders.

In a twenty-third aspect of the present invention, there is provided use of a compound according to any one of (1) to (27) or a pharmacologically acceptable salt or prodrug thereof in the preparation of a medicament for the prophylaxis or treatment of Ophthalmic Disorders.

In an twenty-fourth aspect of the present invention, there is provided a method for the prophylaxis or treatment of a disease in which KCNQ2, KCNQ3 or KCNQ2/3 is involved comprising administering to a patient in need thereof an effective amount of a compound according to any one of (1) to (27) or a pharmacologically acceptable salt or prodrug thereof.

In a twenty-fifth aspect of the present invention, there is provided a method for the prophylaxis or treatment of a condition or disease ameliorated by KCNQ2, KCNQ3 or KCNQ2/3 channel opening comprising administering to a patient in need thereof an effective amount of a compound according to any one of (1) to (27) or a pharmacologically acceptable salt or prodrug thereof.

In a twenty-sixth aspect of the present invention, there is provided a method for the prophylaxis or treatment of Lower Urinary Tract Disorders comprising administering to a patient in need thereof an effective amount of a compound of formula (Ia) as defined in the sixth aspect of the present invention or a pharmacologically acceptable salt or prodrug thereof.

In a twenty-seventh aspect of the present invention, there is provided a method for the prophylaxis or treatment of Anxiety and Anxiety-Related Conditions comprising administering to a patient in need thereof an effective amount of a compound according to any one of (1) to (27) or a pharmacologically acceptable salt or prodrug thereof.

In a twenty-eighth aspect of the present invention, there is provided a method for the prophylaxis or treatment of Epilepsy comprising administering to a patient in need thereof an effective amount of a compound according to any one of (1) to (27) or a pharmacologically acceptable salt or prodrug thereof.

In a twenty-ninth aspect of the present invention, there is provided a method for the prophylaxis or treatment of Pain Disorders comprising administering to a patient in need thereof an effective amount of a compound according to any one of (1) to (27) or a pharmacologically acceptable salt or prodrug thereof.

In a thirtieth aspect of the present invention, there is provided a method for the prophylaxis or treatment of Gynaecological Pain comprising administering to a patient in need thereof an effective amount of a compound of formula (Ia) as defined in the sixth aspect of the present invention or a pharmacologically acceptable salt or prodrug thereof.

In a thirty-first aspect of the present invention, there is provided a method for the prophylaxis or treatment of Cardiac Arrhythmias comprising administering to a patient in need thereof an effective amount of a compound of formula (Ia) as defined in the sixth aspect of the present invention or a pharmacologically acceptable salt or prodrug thereof.

In a thirty-second aspect of the present invention, there is provided a method for the prophylaxis or treatment of Thromboembolic Events comprising administering to a patient in need thereof an effective amount of a compound of formula (Ia) as defined in the sixth aspect of the present invention or a pharmacologically acceptable salt or prodrug thereof.

In a thirty-third aspect of the present invention, there is provided a method for the prophylaxis or treatment of Cardiovascular Diseases comprising administering to a patient in need thereof an effective amount of a compound of formula (Ia) as defined in the sixth aspect of the present invention or a pharmacologically acceptable salt or prodrug thereof.

In a thirty-fourth aspect of the present invention, there is provided a method for the prophylaxis or treatment of Disorders of the Auditory System comprising administering to a patient in need thereof an effective amount of a compound according to any one of (1) to (27) or a pharmacologically acceptable salt or prodrug thereof.

In a thirty-fifth aspect of the present invention, there is provided a method for the prophylaxis or treatment of Migraine comprising administering to a patient in need thereof an effective amount of a compound according to any one of (1) to (27) or a pharmacologically acceptable salt or prodrug thereof.

In a thirty-sixth aspect of the present invention, there is provided a method for the prophylaxis or treatment of Inflammatory and Immunological Diseases comprising administering to a patient in need thereof an effective amount of a compound according to any one of (1) to (27) or a pharmacologically acceptable salt or prodrug thereof.

In a thirty-seventh aspect of the present invention, there is provided a method for the prophylaxis or treatment of Gastrointestinal Disorders comprising administering to a patient in need thereof an effective amount of a compound of formula (Ia) as defined in the sixth aspect of the present invention or a pharmacologically acceptable salt or prodrug thereof.

In a thirty-eighth aspect of the present invention, there is provided a method for the prophylaxis or treatment of Vascular and Visceral Smooth Muscle Disorders comprising administering to a patient in need thereof an effective amount of a compound of formula (Ia) as defined in the sixth aspect of the present invention or a pharmacologically acceptable salt or prodrug thereof.

In a thirty-ninth aspect of the present invention, there is provided a method for the prophylaxis or treatment of Cell Proliferative Disorders comprising administering to a patient in need thereof an effective amount of a compound according to any one of (1) to (27) or a pharmacologically acceptable salt or prodrug thereof.

In a fortieth aspect of the present invention, there is provided a method for the prophylaxis or treatment of Metabolic Disorders comprising administering to a patient in need thereof an effective amount of a compound according to any one of (1) to (27) or a pharmacologically acceptable salt or prodrug thereof.

In a forty-first aspect of the present invention, there is provided a method for the prophylaxis or treatment of Memory Loss comprising administering to a patient in need thereof an effective amount of a compound according to any one of (1) to (27) or a pharmacologically acceptable salt or prodrug thereof.

In a forty-second aspect of the present invention, there is provided a method for the prophylaxis or treatment of CNS-Mediated Motor Dysfunction Disorders comprising administering to a patient in need thereof an effective amount of a compound according to any one of (1) to (27) or a pharmacologically acceptable salt or prodrug thereof.

In a forty-third aspect of the present invention, there is provided a method for the prophylaxis or treatment of Ophthalmic Disorders comprising administering to a patient in need thereof an effective amount of a compound according to any one of (1) to (27) or a pharmacologically acceptable salt or prodrug thereof.

In a forty-fourth aspect of the present invention, there is provided a compound according to any one of (1) to (27) or a pharmacologically acceptable salt or prodrug thereof for use in the prophylaxis or treatment of any disease or condition recited in any one of the fourth, fifth, seventh, eighth, ninth, fourteenth, fifteenth, sixteenth, nineteenth, twentieth, twenty-first, twenty-second and twenty-third aspects of the present invention.

In a forty-fifth aspect of the present invention there is provided a compound of formula (Ia) as defined in the sixth aspect of the present invention or a pharmacologically acceptable salt or prodrug thereof for use in the prophylaxis or treatment of any disease or condition recited in any one of the sixth, tenth, eleventh, twelfth, thirteenth, seventeenth and eighteenth aspects of the present invention.

In a forty-sixth aspect of the present invention there is provided a pharmaceutical composition comprising a pharmacologically acceptable diluent or carrier and an active ingredient, wherein said active ingredient is a compound according to any one of (1) to (27) or a pharmacologically acceptable salt or prodrug thereof for use in the prophylaxis or treatment of any disease or condition recited in any one of the fourth, fifth, seventh, eighth, ninth, fourteenth, fifteenth, sixteenth, nineteenth, twentieth, twenty-first, twenty-second and twenty-third aspects of the present invention.

In the forty-seventh aspect of the present invention there is provided a pharmaceutical composition comprising a pharmacologically acceptable diluent or carrier and an active ingredient, wherein said active ingredient is a compound of formula (Ia) as defined in the sixth aspect of the present invention or a pharmacologically acceptable salt or prodrug thereof for use in the prophylaxis or treatment of any disease or condition recited in any one of the sixth, tenth, eleventh, twelfth, thirteenth, seventeenth and eighteenth aspects of the present invention.

In a forty-eighth aspect of the present invention there is provided a pharmaceutical composition comprising a pharmacologically acceptable diluent or carrier and at least two active ingredients, wherein said active ingredients comprise at least one compound according to any one of (1) to (27) or at least one compound of formula (Ia) as defined in the sixth aspect of the present invention, or a pharmacologically acceptable salt or prodrug thereof in combination with at least one compound selected from the group consisting of muscarinic receptor antagonists, β3 adrenergic receptor agonists, neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), 5-HT antagonists, alpha-1 adrenoceptor antagonists, tricyclic antidepressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs).

Preferred pharmaceutical combinations according to the forty-eighth aspect of the present invention include:

(1) a pharmaceutical composition comprising a pharmacologically acceptable diluent or carrier and a combination of active ingredients, wherein said active ingredients comprise at least one compound according to any one of (1) to (27) or at least one compound of formula (Ia) as defined in the sixth aspect of the present invention, or a pharmacologically acceptable salt or prodrug thereof in combination with at least one compound selected from the group consisting of muscarinic receptor antagonists, β3 adrenergic receptor agonists, neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), 5-HT antagonists and α-1 adrenoceptor antagonists; and (2) a pharmaceutical composition comprising a pharmacologically acceptable diluent or carrier and a combination of active ingredients, wherein said active ingredients comprise at least one compound according to any one of (1) to (27) or at least one compound of formula (Ia) as defined in the sixth aspect of the present invention, or a pharmacologically acceptable salt or prodrug thereof in combination with at least one compound selected from the group consisting of neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), tricyclic antidepressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs).

The combinations of preferred option (1) are of particular use in the prophylaxis or treatment of lower urinary tract disorders. The combinations of preferred option (2) are of particular use in the prophylaxis or treatment of pain.

In a forty-ninth aspect of the present invention there is provided use of at least one compound according to any one of (1) to (27) or at least one compound of formula (Ia) as defined in the sixth aspect of the present invention, or a pharmacologically acceptable salt or prodrug thereof and at least one compound selected from the group consisting of muscarinic receptor antagonists, β3 adrenergic receptor agonists, neurokinin K receptor antagonists, vanilloid VR1 agonists, calcium channel α2 δ delta ligands, potassium channel inhibitors, calcium channel inhibitors, sodium channel blockers, serotonin and norepinephrine reuptake inhibitors (SNRIs), 5-HT antagonists and α-1 adrenoceptor antagonists in the manufacture of a medicament for the prophylaxis or treatment of lower urinary tract disorders.

In a fiftieth aspect of the present invention there is provided use of at least one compound according to any one of (1) to (27) or at least one compound of formula (Ia) as defined in the sixth aspect of the present invention, or a pharmacologically acceptable salt or prodrug thereof and at least one compound selected from the group consisting of neurokinin K receptor antagonists, vanilloid VR1 agonists, calcium channel α2 δ delta ligands, potassium channel inhibitors, calcium channel inhibitors, sodium channel blockers, serotonin and norepinephrine reuptake inhibitors (SNRIs), tricyclic antidepressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs) in the manufacture of a medicament for the prophylaxis or treatment of pain.

In a fifty-first aspect of the present invention there is provided a pharmaceutical composition according to the forty-eighth aspect of the present invention for the prophylaxis or treatment of any disease or condition recited in the fourth to twenty-third aspects of the present invention.

DETAILED DESCRIPTION OF THE INVENTION

In the compounds of formula (I) and (Ia) of the present invention, the alkyl groups in the definitions of $R^1$, $R^2$, $R^{3a}$, $R^{3b}$, $R^{4a}$, $R^{4b}$, $R^{5a}$, $R^{5b}$, $R^{6a}$, $R^{6b}$, $R^{6c}$, $R^{6d}$ and X are preferably alkyl groups having from 1 to 6 carbon atoms, more preferably alkyl groups having from 1 to 4 carbon atoms and most preferably methyl groups.

In the compounds of formula (I) and (Ia) of the present invention, the cycloalkyl groups in the definitions of $R^{3a}$, $R^{3b}$, $R^{4a}$, $R^{4b}$, $R^{5a}$, $R^{6b}$ and X are preferably cycloalkyl groups having from 3 to 7 carbon atoms, more preferably having 5 or 6 carbon atoms and most preferably cyclohexyl.

In the compounds of formula (I) and (Ia) of the present invention, the aryl groups in the definitions of $Ar^1$, $Ar^2$, $R^{3a}$, $R^{3b}$, $R^{4a}$, $R^{4b}$, $R^{5a}$ and X are preferably aryl groups having from one to 5 to 14 carbon atoms. Examples of the unsubstituted aryl groups include phenyl, indenyl, naphthyl, phenanthrenyl and anthracenyl groups. More preferred aryl groups include phenyl groups.

In the compounds of formula (I) and (Ia) of the present invention, the heteroaryl groups in the definitions of $Ar^1$, $Ar^2$, $R^{3a}$, $R^{3b}$, $R^{4a}$, $R^{4b}$, $R^{5a}$, $R^{5b}$ and X are preferably 5- to 7-membered aromatic heterocyclic group containing 1 to 3 sulfur atoms, oxygen atoms and/or nitrogen atoms. Examples include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl groups. More preferred heteroaryl groups include furyl, thienyl, pyrrolyl and pyridyl.

In the compounds of formula (I) and (Ia) of the present invention, the alkoxy groups in the definitions of $R^1$, $R^2$ and X are preferably alkoxy groups having from 1 to 6 carbon atoms, more preferably alkoxy groups having from 1 to 4 carbon atoms and most preferably methoxy or ethoxy groups.

In the compounds of formula (I) and (Ia) of the present invention, the haloalkoxy groups in the definitions of $R^1$, $R^2$ and X are preferably alkoxy groups as defined above that are substituted with one or more halogen atoms. More preferably, they are alkoxy groups having from 1 to 4 carbon atoms that are substituted with at least one chlorine or fluorine atom and most preferably they are chloromethoxy groups, trichloromethoxy groups, trifluoromethoxy groups and tetrafluoroethoxy groups.

In the compounds of formula (I) and (Ia) of the present invention, the haloalkyl groups in the definitions of $R^1$, $R^2$ and X are preferably alkyl groups as defined above that are substituted with one or more halogen atoms. More preferably, they are alkyl groups having from 1 to 4 carbon atoms that are substituted with at least one chlorine or fluorine atom and most preferably they are chloromethyl groups, trichloromethyl groups, trifluoromethyl groups and tetrafluoroethyl groups.

In the compounds of formula (I) and (Ia) of the present invention, the alkoxycarbonyl groups in the definitions of $R^1$, $R^2$ and X are preferably carbonyl groups substituted with alkoxy groups as defined above, and are more preferably methoxycarbonyl or ethoxycarbonyl groups.

In the compounds of formula (I) and (Ia) of the present invention, the hydroxyalkyl groups in the definitions of X are preferably alkyl groups as defined above that are substituted with one ore more hydroxy groups, and are more preferably hydroxymethyl, 1-hydroxyethyl or 2-hydroxyethyl groups.

In the compounds of formula (I) and (Ia) of the present invention, the monoalkylamino groups in the definitions of $R^1$, $R^2$ and X are preferably amino groups which are substituted with one alkyl group as defined above, and are more preferably methylamino, ethylamino or t-butylamino groups.

In the compounds of formula (I) and (Ia) of the present invention, the dialkylamino groups in the definitions of $R^1$, $R^2$ and X are preferably amino groups which are substituted with two alkyl groups as defined above which may be the same or different from each other, and are more preferably dimethylamino or diethylamino groups.

In the compounds of formula (I) and (Ia) of the present invention, the acylamino groups in the definitions of $R^1$ and $R^2$ are preferably amino groups which are substituted with an acyl group having from 1 to 6 carbon atoms and are more preferably acetylamino or propionylamino groups.

In the compounds of formula (I) and (Ia) of the present invention, the alkoxycarbonylamino groups in the definitions of $R^1$ and $R^2$ are preferably amino groups which are substituted with an alkoxycarbonyl group as defined above, and are more preferably methoxycarbonylamino or ethoxycarbonylamino groups.

In the compounds of formula (I) and (Ia) of the present invention, the alkylsulphonyl groups in the definitions of $R^1$ and $R^2$ are preferably sulphonyl groups which are substituted with an alkyl group as defined above and are more preferably a methylsulphonyl or ethylsulphonyl group.

In the compounds of formula (I) and (Ia) of the present invention, the alkylsulphonylamino groups in the definitions of $R^1$ and $R^2$ are preferably sulphonylamino groups which are substituted with an alkyl group as defined above and are more preferably a methylsulphonylamino or ethylsulphonylamino group.

In the compounds of formula (I) and (Ia) of the present invention, the polyalkylene glycol residues in the definition of X are preferably groups of formula HO—[$(CR^{6a}R^{6b})_{c1}$—O—$(CR^{6c}R^{6d})_{c2}]_{c3}$— wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different and each is a hydrogen atom or an alkyl group having from 1 to 6 carbon atoms; more preferably groups of formula HO—[$(CR^{6a}R^{6b})_{c1}$—O—$(CR^{6c}R^{6d})_{c2}]_{c3}$—, wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different and each is a hydrogen atom or an alkyl group having from 1 to 4 carbon atoms; and most preferably groups of formula HO—[$(CR^{6a}R^{6b})_{c1}$—O—$(CR^{6c}R^{6d})_{c2}]_{c3}$—, wherein c1 and c2 are the same or different and each is 1 or 2, c3 is an integer of from 1 to 6 and each of $R^{6a}$, $R^{6b}$, $R^{6c}$ and $R^{6d}$ is the same or different and is a hydrogen atom.

In the compounds of formula (I) and (Ia) of the present invention, the alkoxyalkyl groups in the definition of X are preferably alkyl groups as defined above that are substituted by alkoxy groups as defined above, and are more preferably methoxymethyl groups, 2-methoxyethyl groups or 2-ethoxyethyl groups.

In the compounds of formula (I) and (Ia) of the present invention, the haloalkoxyalkyl groups in the definition of X are preferably alkyl groups as defined above that are substituted by haloalkoxy groups having from 1 to 6 carbon atoms, and are more preferably difluoromethoxymethyl groups, trichloromethoxymethyl groups, 2-trichloromethoxyethyl groups or 2-tetrafluoroethoxyethyl groups.

In the compounds of formula (I) and (Ia) of the present invention, the aryloxyalkyl groups in the definition of X are preferably alkyl groups as defined above that are substituted by aryloxy groups comprising aryl groups as defined above that are attached to an oxygen atom, and are more preferably phenoxymethyl groups or 2-phenoxyethyl groups.

In the compounds of formula (I) and (Ia) of the present invention, the alkyl groups that are substituted with groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms in the definition of X are preferably alkyl groups that are substituted with groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms comprising an alkyl group having form 1 to 6 carbon atoms that is substituted with a group of formula NR8R9 wherein R8 and R9 together with the nitrogen atom to which they are attached form a 4- to 14-membered nitrogen-containing saturated or partially unsaturated heterocyclic group having one or more rings (including bridged saturated or partially unsaturated heterocyclic groups having one or more rings), which optionally further contains one or more additional nitrogen, oxygen or sulphur atoms (wherein said saturated or partially unsaturated heterocyclic group is optionally substituted by one or more substituents selected from the group consisting of alkyl groups as defined above, halogen atoms, haloalkyl groups as defined above, alkoxy groups as defined above, alkoxycarbonyl groups as defined above, carboxyl groups, nitro groups, amino groups, monoalkylamino groups as defined above, dialkylamino groups as defined above and hydroxyl groups), and more preferably piperazin-1-yl groups, 4-methylpiperazin-1-yl groups, morpholin-4-yl, 3-hydroxy-pyrrolidin-1-yl, 4,4-difluoro-piperidin-1-yl and 4-methoxycarbonylpiperazin-1-yl groups.

In the compounds of formula (I) and (Ia) of the present invention, the aminoalkyl groups in the definition of X are preferably alkyl groups as defined above that are substituted with one ore more amino groups, and are more preferably aminomethyl, 1-aminoethyl or 2-aminoethyl groups.

In the compounds of formula (I) and (Ia) of the present invention, the monoalkylaminoalkyl groups in the definition of X are preferably alkyl groups as defined above that are substituted with one ore more monoalkylamino groups as defined above, and are more preferably methylaminomethyl, ethylaminomethyl, 1-methylaminoethyl or 2-methylaminoethyl groups.

In the compounds of formula (I) and (Ia) of the present invention, the dialkylaminoalkyl groups in the definition of X are preferably alkyl groups as defined above that are substituted with one ore more dialkylamino groups as defined above, and are more preferably dimethylaminomethyl or 2-dimethylaminoethyl groups.

In the compounds of formula (I) and (Ia) of the present invention, the carboxyalkyl groups in the definition of X are preferably alkyl groups as defined above that are substituted with one ore more carboxy groups, and more preferably carboxymethyl groups or 2-carboxyethyl groups.

In the compounds of formula (I) and (Ia) of the present invention, the alkoxycarbonylalkyl groups in the definition of X are preferably alkyl groups as defined above that are substituted with alkoxycarbonyl groups as defined above, and are more preferably methoxycarbonylmethyl groups, ethoxycarbonylmethyl groups, 2-methoxycarbonylethyl groups or 2-ethoxycarbonylethyl groups.

In the compounds of formula (I) and (Ia) of the present invention, the haloalkoxycarbonylalkyl groups in the definition of X are preferably alkyl groups as defined above that are substituted with haloalkoxycarbonyl groups comprising alkoxycarbonyl groups as defined above wherein the alkoxy moiety is substituted with one or more halogen atoms, and are more preferably dichloromethoxycarbonylmethyl groups, pentafluoroethoxycarbonylmethyl groups, 2-trichloromethoxycarbonylethyl groups or 2-tetrafluoroethoxycarbonylethyl groups.

In the compounds of formula (I) and (Ia) of the present invention, the aralkyloxycarbonylalkyl groups in the definition of X are preferably alkyl groups as defined above that are substituted with aralkyloxycarbonyl groups comprising alkyl groups as defined above that are substituted by aryl groups as defined above which are bonded to an oxycarbonyl moiety, and more preferably benzyloxycarbonylmethyl groups and 2-benzyloxycarbonylethyl groups.

The compounds of formula (I) and (Ia) of the present invention can form pharmacologically acceptable salts and these form a part of the present invention. Examples of such salts include inorganic salts such as ammonium salts; organic amine salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-N-phenethylamine salts, piperazine salts, tetramethylammonium salts and tris(hydroxymethyl) aminemethane salts; hydrohalogenated salts such as hydrofluoric acid salts, hydrochlorides, hydrobromides and hydroiodides; inorganic acid salts such as nitrates, perchlorates, sulfates and phosphates; lower alkanesulfonate salts such as methanesulfonates, trifluoromethanesulfonates and ethanesulfonates; arylsulfonate salts such as benzensulfonates and p-toluenesulfonates; organic acid salts such as acetates, malates, fumarates, succinates, citrates, tartrates, oxalates and maleates; and amino acid salts such as ornithinates, glutamates and aspartates. Of these, organic amine salts are more preferred and triethylamine salts are most preferred.

The compounds of formula (I) and (Ia) of the present invention can be administered in the form of prodrugs. Prodrugs are derivatives of the pharmacologically active compound in which one or more of the substituents on said compound are protected by a group which is then removable by a biological process (e.g. hydrolysis) in vivo after administration to the patient. Many suitable prodrugs are well-known to the person in the art and can be found, for example, in "Greene's Protective Groups in Organic Synthesis", $4^{th}$ Edition, 2006, Wiley-VCH. Suitable examples of such prodrugs include pharmacologically acceptable esters of the compound having the formula (I) or (Ia) wherein a carboxyl moiety of the compound having the formula (I) or (Ia) is esterified. The pharmacologically acceptable esters are not particularly restricted, and can be selected by a person with an ordinary skill in the art. In the case of said esters, it is preferable that such esters can be cleaved by a biological process such as hydrolysis in vivo. The group constituting the said esters (the group shown as R when the esters thereof are expressed as —COOR) can be, for example, a $C_1$-$C_4$ alkoxy $C_1$-$C_4$ alkyl group such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, propoxymethyl, isopropoxymethyl, butoxymethyl or t-butoxymethyl; a $C_1$-$C_4$ alkoxylated $C_1$-$C_4$ alkoxy $C_1$-$C_4$ alkyl group such as 2-methoxyethoxymethyl; a $C_6$-$C_{10}$ acyloxy $C_1$-$C_4$ alkyl group such as phenoxymethyl; a halogenated $C_1$-$C_4$ alkoxy $C_1$-$C_4$ alkyl group such as 2,2,2-trichloroethoxymethyl or bis(2-chloroethoxy)methyl; a $C_1$-$C_4$ alkoxycarbonyl $C_1$-$C_4$ alkyl group such as methoxycarbonylmethyl; a cyano $C_1$-$C_4$ alkyl group such as cyanomethyl or 2-cyanoethyl; a $C_1$-$C_4$ alkylthiomethyl group such as methylthiomethyl or ethylthiomethyl; a $C_6$-$C_{10}$ arylthiomethyl group such as phenylthiomethyl or naphthylthiomethyl; a $C_1$-$C_4$ alkylsulfonyl $C_1$-$C_4$ lower alkyl group, which may be optionally substituted with a halogen atom(s) such as 2-methanesulfonylethyl or 2-trifluoromethanesulfonylethyl; a $C_6$-$C_{10}$arylsulfonyl $C_1$-$C_4$ alkyl group such as 2-benzenesulfonylethyl or 2-toluenesulfonylethyl; a $C_1$-$C_7$ aliphatic acyloxy $C_1$-$C_4$ alkyl group such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl; a $C_5$-$C_6$ cycloalkylcarbonyloxy $C_1$-$C_4$ alkyl group such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl; a $C_6$-$C_{10}$ arylcarbonyloxy $C_1$-$C_4$ alkyl group such as benzoyloxymethyl; a $C_1$-$C_6$ alkoxycarbonyloxy $C_1$-$C_4$ alkyl group such as methoxycarbonyloxymethyl, 1-(methoxycarbonyloxy)ethyl, 1-(methoxycarbonyloxy)propyl, 1-(methoxycarbonyloxy)butyl, 1-(methoxycarbonyloxy)pentyl, 1-(methoxycarbonyloxy)hexyl, ethoxycarbonyloxymethyl, 1-(ethoxycarbonyloxy)ethyl, 1-(ethoxycarbonyloxy)propyl, 1-(ethoxycarbonyloxy)butyl, 1-(ethoxycarbonyloxy)pentyl, 1-(ethoxycarbonyloxy)hexyl, propoxycarbonyloxymethyl, 1-(propoxycarbonyloxy)ethyl, 1-(propoxycarbonyloxy)propyl, 1-(propoxycarbonyloxy)butyl, isopropoxycarbonyloxymethyl, 1-(isopropoxycarbonyloxy)ethyl, 1-(isopropoxycarbonyloxy)butyl, butoxycarbonyloxymethyl, 1-(butoxycarbonyloxy)ethyl, 1-(butoxycarbonyloxy)propyl, 1-(butoxycarbonyloxy)butyl, isobutoxycarbonyloxymethyl, 1-(isobutoxycarbonyloxy)ethyl, 1-(isobutoxycarbonyloxy) propyl, 1-(isobutoxycarbonyloxy)butyl, t-butoxycarbonyloxymethyl, 1-(t-butoxycarbonyloxy)ethyl, pentyloxycarbonyloxymethyl, 1-(pentyloxycarbonyloxy)ethyl, 1-(pentyloxycarbonyloxy)propyl, hexyloxycarbonyloxymethyl, 1-(hexyloxycarbonyloxy)ethyl or 1-(hexyloxycarbonyloxy)propyl; a $C_5$-$C_6$ cycloalkyloxycarbonyloxy $C_1$-$C_4$ alkyl group such as cyclopentyloxycarbonyloxymethyl, 1-(cyclopentyloxycarbonyloxy)ethyl, 1-(cyclopentyloxycarbonyloxy)propyl, 1-(cyclopentyloxycarbonyloxy)butyl, cyclohexyloxycarbonyloxymethyl, 1-(cyclohexyloxycarbonyloxy)ethyl, 1-(cyclohexyloxycarbonyloxy)propyl or 1-(cyclohexyloxycarbonyloxy)butyl; a [5-($C_1$-$C_4$ alkyl)-2-oxo-1,3-dioxolen-4-yl]methyl group such as (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methy; a [5-(phenyl, which may be optionally substituted with a $C_1$-$C_4$ alkyl, $C_1$-$C_4$ alkoxy or halogen atom(s))-2-oxo-1,3-dioxolen-4-yl]methyl group such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl or [5-(4-chlorophenyl)-2-oxo-1,3-dioxolen-4-yl]methyl; or a phthalidyl group, which may be optionally substituted with a $C_1$-$C_4$ alkyl or $C_1$-$C_4$ alkoxy group(s), such as phthalidyl, dimethylphthalidyl or dimethoxyphthalidyl, and is preferably a pivaloyloxymethyl group, phthalidyl group or (5-methyl-2-oxo-1,3-dioxolen-4-yl)methyl group, and more preferably a (5-methyl-2-oxo-1,3-dioxolen-4-yl)methyl group.

The compounds of formula (I) and (Ia) or pharmacologically active prodrugs or salts thereof contain some substituents for which there exist isosteres, and compounds containing such isosteres in place of said substituents also form a part of the present invention. For example, where the compounds of formula (I) and (Ia) or pharmacologically active prodrugs or salts thereof contain a carboxyl group, this can be replaced with a tetrazolyl group.

Hydrates or solvates of the compounds of formula (I) and (Ia), prodrugs thereof and pharmacologically acceptable salts thereof can also be used and form a part of the invention.

Some compounds of formula (I) and (Ia) and their pharmacologically acceptable salts or prodrugs thereof of the present invention may have one or more asymmetric carbons, and optical isomers (including diastereoisomers) due to the presence of asymmetric carbon atom(s) in the molecule can exist. These respective isomers are included in the present invention, both as individual isomers and mixtures thereof in all possible ratios.

Examples of the administration form of a compound having the general formula (I) and (Ia) of the present invention, or pharmacologically acceptable salt or prodrug thereof, include oral administration by tablets, capsules, granules, powders or syrups, and parenteral administration by injection, patches or suppositories. Moreover, a compound having the general formula (I) and (Ia) or a pharmacologically acceptable salt or prodrug thereof of the present invention can also be administered by pulmonary administration in the form of a powder, solution or suspension. Preparations for these administrations are produced by known methods using additives such as excipients, lubricants, binders, disintegrants, stabilizers, corrigents, diluents and so forth.

Examples of excipients include organic excipients such as sugar derivatives, e.g. lactose, sucrose, glucose, mannitol or sorbitol, starch derivatives, e.g. corn starch, potato starch, α-starch, dextrin or carboxymethyl starch, cellulose derivatives, e.g. crystalline cellulose, low substituted hydroxypropyl cellulose, hydroxypropyl methyl cellulose, carboxymethyl cellulose, calcium carboxymethyl cellulose or internally crosslinked sodium carboxymethyl cellulose, and gum Arabic, dextran or pullulan; and, inorganic excipients such as silicate derivatives, e.g. light anhydrous silicic acid, synthetic aluminium silicate or magnesium aluminium metasilicate, phosphates, e.g. calcium phosphate, carbonates, e.g. calcium carbonate, or sulfates, e.g. calcium sulfate.

Examples of lubricants include stearic acid and metal stearates such as calcium stearate or magnesium stearate; talc; colloidal silica; waxes such as bee gum or spermaceti; boric acid; adipic acid; sulfates such as sodium sulfate; glycol; fumaric acid; sodium benzoate; DL-leucine; sodium fatty acid salts; lauryl sulfates such as sodium lauryl sulfate or magnesium lauryl sulfate; silicic acids such as silicic anhydride or silicate hydrate; and, starch derivatives.

Examples of binders include polyvinylpyrrolidone, Macrogol and compounds similar to the aforementioned excipients.

Examples of disintegrants agents include compounds similar to the aforementioned excipients, and chemically crosslinked starches and celluloses such as cross sodium carmellose, sodium carboxymethyl starch or crosslinked polyvinylpyrrolidone.

Examples of stabilizers include paraoxybenzoate esters such as methyl paraben or propyl paraben; alcohols such as chlorobutanol, benzyl alcohol or phenyl ethyl alcohol; benzalkonium chloride; phenols such as phenol or cresol; thimerosal; dehydroacetic acid; and, sorbic acid.

Examples of corrigents include ordinarily used sweeteners, sour flavourings and fragrances.

In the case of producing a solution or suspension for pulmonary administration of a compound having the general formula (I) and (Ia) or pharmacologically acceptable salt or prodrug thereof of the present invention, for example, said solution or suspension can be produced by dissolving or suspending crystals of the present invention in water or in a mixture of water and an auxiliary solvent (e.g. ethanol, propylene glycol or polyethylene glycol). Such a solution or suspension may also contain an antiseptic (e.g. benzalkonium chloride), solubilizing agent (e.g. a polysorbate such as Tween 80 or Span 80 or surface activator such as benzalkonium chloride), buffer, isotonic agent (e.g. sodium chloride), absorption promoter and/or thickener. In addition, the suspension may additionally contain a suspending agent (such as microcrystalline cellulose or sodium carboxymethyl cellulose).

A composition for pulmonary administration produced in the manner described above is administered directly into the nasal cavity or oral cavity by a typical means in the field of inhalants (using, for example, a dropper, pipette, cannula or atomizer). In the case of using an atomizer, crystals of the present invention can be atomized as an aerosol in the form of a pressurized pack together with a suitable nebula (for example, a chlorofluorocarbon such as dichlorofluoromethane, trichlorofluoromethane or dichlorotetrafluoroethane, or a gas such as carbon dioxide), or they can be administered using a nebulizer.

The amount of a compound having the general formula (I) and (Ia) or pharmacologically acceptable salt or prodrug thereof of the present invention used varies depending on the symptoms, age, administration method and so forth, and may be administered either in a single dose or by dividing into multiple doses according to the symptoms.

In the combinations according to the forty-seventh aspect of the present invention, typical examples of each of the classes of compounds that can be used in combination with the compounds having the general formula (I) and (Ia) or a pharmacologically acceptable salt or prodrug thereof of the present invention are as follows:

1. Examples of muscarinic receptor antagonists (including but not limited to selective M3 antagonists) include esoxybutynin, oxybutynin [especially the chloride], tolterodine [especially the tartrate], solifenacin [especially the succinate], darifenacin [especially the hydrobromide], temiverine, fesoterodine, imidafenacin and trospium [especially the chloride].
2. Examples of β3 adrenergic receptor agonists include YM-178 and solabegron, KUC-7483.
3. Examples of neurokinin K receptor antagonists (including selective NK-1 antagonists) include cizolirtine and casopitant.
4. Examples of vanilloid VR1 agonists include capsaicin, resiniferatoxin and NDG-8243.
5. Examples of calcium channel α2 δ ligands include gabapentin and pregabalin.
6. Examples of potassium channel activators (including activators of KCNQ, BKCa channels, Kv channels and KATP channels) include KW-7158, NS-8 and retigabine.
7. Examples of calcium channel inhibitors (including Cav2.2 channel inhibitors) include ziconotide and NMED-160.
8. Examples of sodium channel blockers include lidocaine, lamotrigine, VX-409, ralfinamide and carbamazepine.
9. Examples of serotonin and norepinephrine reuptake inhibitors (SNRIs) include duloxetine and venlafaxine
10. Examples of 5-HT antagonists including 5-HT1a antagonists and 5HT3 antagonists.
11. Examples of α-1 adrenoceptor antagonists include tamsulosin.
12. Examples of tricyclic antidepressants include amitriptyline, amoxapine, clomipramine, dosulepin (dothiepin), doxepin, imipramine, lofepramine, nortriptyline, and trimipramine
13. Examples of N-methyl-D-aspartate (NMDA) receptor antagonists include ketamine, memantine, amantadine, AVP-923, NP-1 and EVT-101.

14. Examples of cannabinoid receptor agonists include GW-1000 (Sativex) and KDS-2000.
15. Anti-convulsants. Examples include lacosamide, carbamazepine, topiramate, oxcarbazepine and levetiracetam
16. Examples of aldose reductase inhibitors include tolrestat, zopolrestat, zenarestat, epalrestat, sorbinil, AS-3201, fidarestat, risarestat, ponalrestat and alrestatin.
17. Examples of opioids (e.g. mu opioid agonists) include fentanyl and tapentadol.
18. Examples of a adrenoceptor agonists include $a_1$ adrenoceptor agonists such as ethoxamine, phenylephrine, oxymetazoline, tetrahydralazine and xylometazoline and $a_2$-adrenoceptor agonists such as clonidine, guanabenz, guanfacine and α-methyldopa.
19. Examples of P2X receptor antagonists including P2X2 receptor antagonists and P2X7 receptor antagonists.
20. Examples of acid-sensing ion channel modulators include amiloride.
21. Examples of NGF receptor modulators include trkA.
22. Examples of nicotinic acetylcholine receptor modulators include A-85380, tebanicline, ABT-366833, ABT-202, ABT-894, epibatidine analogs and SIB-1663.
23. Examples of synaptic vesicle protein 2A ligands include brivaracetam.

Examples of the administration form of the combination of the present invention are the same as given above for the compounds of general formula (I) and (Ia) and pharmacologically acceptable salts thereof. The particular form can be chosen depending upon the condition to be treated and the nature of the compounds being administered in combination. For example, a combination of a compound of general formula (I) and (Ia) or a pharmacologically acceptable salt or prodrug thereof with lidocaine could be administered transdermally by means of a patch while a combination with ziconotide could be administered transmucosally.

Synthesis of the Compounds of the Invention

Compounds of formula (I) or (Ia) (the schemes below are given for compounds of formula (I)) wherein $Ar^1$ and $Ar^2$ each represent phenyl groups, W is a group of formula NH, Y and Z are each single bonds and V is a group of formula —$(CR^{3a}R^{3b})_p$CONR$^{3b}$X wherein X is defined as above can be prepared according to the following general Reaction Schemes:

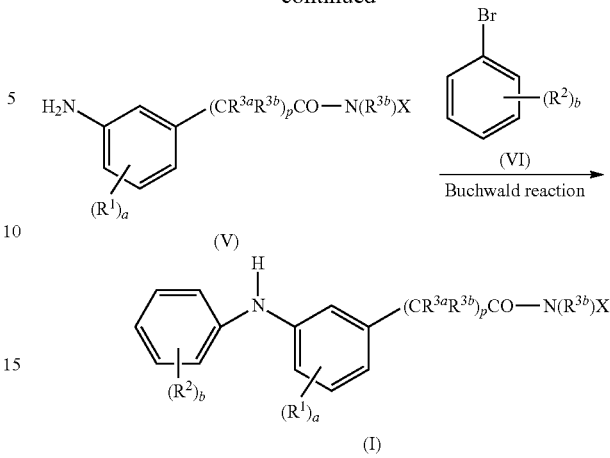

wherein $R^1$, $R^2$, $R^{3a}$, $R^{3b}$, X and p are as defined above.

The first step of Reaction Scheme 1 involves reaction of a 3-nitrophenylacetic acid derivative of formula (II) which has a leaving group L with an amino compound of formula (III) to give a 3-nitrophenylmethylamide derivative of formula (IV). The leaving group L can be any group which readily becomes detached from the carbonyl group to which it is attached in the compound of formula (II) on nucleophilic attack by the nitrogen atom of the amino compound of formula (III). Such leaving groups are well known to the person skilled in the art and include halogen atoms, mesyl groups, tosyl groups and trifluoromethanesulfonyl groups. Chlorine atoms, iodine atoms, bromine atoms and tosyl groups are more preferred and chlorine atoms are most preferred.

The second step of Reaction Scheme 1 involves reaction of the 3-nitrophenylmethylamide derivative of formula (IV) with a reducing agent to give a 3-aminophenylmethylamide derivative of formula (V). Any reducing agent suitable for the reduction of a nitro group to an amino group may be used, suitable examples of which include catalytic hydrogenation, the zinc-acetic acid method, the tin-alcohol method and the tin-hydrochloric acid method. Preferred is catalytic hydrogenation.

The final step of Reaction Scheme 1 involves reaction of the 3-aminophenylmethylamide derivative of formula (V) with an optionally substituted bromophenyl compound of formula (VI) in a Buchwald reaction to give the target N-phenyl-aminophenylmethylamide derivative of formula (I).

Reaction Scheme 1

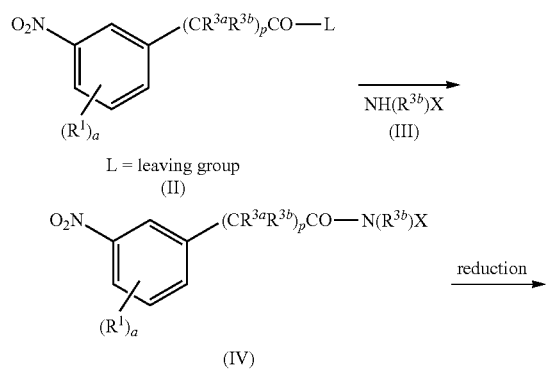

Reaction Scheme 2

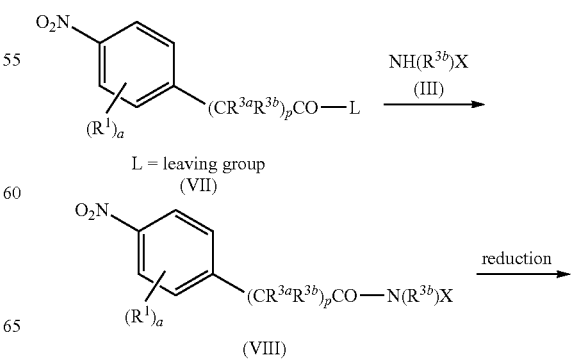

-continued

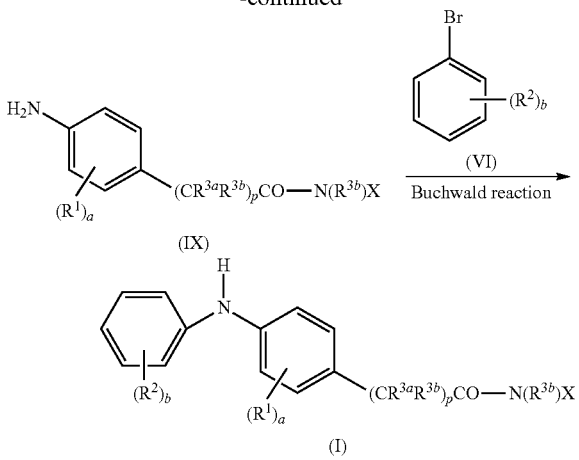

wherein $R^1$, $R^2$, $R^{3a}$, $R^{3b}$, X and p are as defined above.

The first step of Reaction Scheme 2 involves reaction of a 4-nitrophenylacetic acid derivative of formula (VII) which has a leaving group L with an amino compound of formula (III) to give a 4-nitrophenylmethylamide derivative of formula (VIII). The leaving group L can be any group which readily becomes detached from the carbonyl group to which it is attached in the compound of formula (VII) on nucleophilic attack by the nitrogen atom of the amino compound of formula (III). Such leaving groups are well known to the person skilled in the art and include halogen atoms, mesyl groups, tosyl groups and trifluoromethanesulfonyl groups. Chlorine atoms, iodine atoms, bromine atoms and tosyl groups are more preferred and chlorine atoms are most preferred.

The second step of Reaction Scheme 2 involves reaction of the 4-nitrophenylmethylamide derivative of formula (VIII) with a reducing agent to give a 4-aminophenylmethylamide derivative of formula (IX). Any reducing agent suitable for the reduction of a nitro group to an amino group may be used, suitable examples of which include catalytic hydrogenation, the zinc-acetic acid method, the tin-alcohol method and the tin-hydrochloric acid method. Preferred is catalytic hydrogenation.

The final step of Reaction Scheme 2 involves reaction of the 4-aminophenylmethylamide derivative of formula (IX) with an optionally substituted bromophenyl compound of formula (VI) in a Buchwald reaction to give the target N-phenyl-aminophenylmethylamide derivative of formula (I).

EXAMPLES

Using the general procedure described above in Reaction Scheme 1, the following compounds were prepared.

Example 1

N-(2-Hydroxy-ethyl)-2-[3-(2,4,6-trichloro-phenylamino)-phenyl]-acetamide

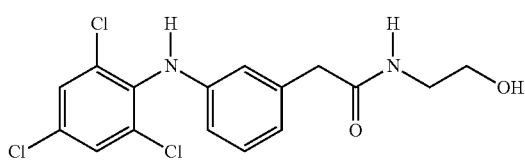 [SMILES: O=C(Cc1cccc(Nc2c(Cl)cc(Cl)cc2Cl)c1)NCCO]

(3-Nitrophenyl)-acetic acid 2,5-dioxopyrrolidin-1-yl ester

To a stirred solution of 3-nitrophenyl acetic acid (1.00 g, 5.53 mmol) and dimethylformamide (catalytic, 3 drops) in dichloromethane (50 ml) was added oxalyl chloride (0.59 ml, 6.91 mmol) dropwise via syringe and the reaction stirred at room temperature for 30 minutes. N-hydroxysuccinamide (0.667 g, 5.80 mmol) and triethylamine (1.92 ml, 13.81 mmol) were added in one portion and the reaction left to stir at room temperature overnight. The reaction was washed with water, separated, the organic layer dried over sodium sulfate, filtered and concentrated onto silica in vacuo. The reaction was purified by column chromatography eluting with 5% MeOH:DCM to afford the named product (0.937 g). $R_f$ (2% MeOH:DCM) 0.10; LCMS $R_t$=3.43 min, m/z (ES+) 296 (M+$H_2O$).

N-(2-Hydroxyethyl)-2-(3-nitrophenyl)acetamide

To a stirred solution of (3-nitrophenyl)-acetic acid 2,5-dioxopyrrolidin-1-yl ester (0.465 g, 1.67 mmol) in acetonitrile (10 ml) was added 2-aminoethanol (111 µL, 1.84 mmol) in one portion and the reaction left to stir at room temperature overnight. The reaction was filtered, concentrated onto silica in vacuo and purified by column chromatography eluting with 10% MeOH:DCM to afford the named product (0.205 g). $R_f$ (5% MeOH:DCM) 0.13; LCMS $R_t$=2.04 min, m/z (ES+) 225 (M+H).

2-(3-Aminophenyl)-N-(2-hydroxyethyl)-acetamide

To a stirred solution of N-(2-hydroxyethyl)-2-(3-nitrophenyl)acetamide (0.205 g, 0.92 mmol) in methanol (10 ml) under an atmosphere of nitrogen was added 10% Pd/C (10 Wt %, 20 mg) in one portion. The reaction was evacuated, placed under an atmosphere of hydrogen (1 bar) and stirred vigorously overnight. The reaction was filtered through celite and the filtrate concentrated in vacuo. The crude mixture was purified using an SCX solid phase extraction cartridge eluting with 10% MeOH:DCM to afford the named product (0.175 g). LCMS $R_t$=1.30 min, m/z (ES+) 195 (M+H).

N-(2-Hydroxyethyl)-2-[3-(2,4,6-trichlorophenylamino)phenyl]-acetamide

To a stirred solution of 2-(3-aminophenyl)-N-(2-hydroxyethyl)-acetamide (0.09 g, 0.46 mmol), 2,4,6-trichloro-1-bromobenzene (0.151 g, 0.46 mmol), $K_2CO_3$ (0.160 g, 1.15 mmol) and xantphos (0.027 g, 0.046 mmol) in 1,4-dioxane (2 ml) under nitrogen in a microwave tube was added $Pd_2dba_3$ (0.021 g, 0.023 mmol) in one portion and the tube sealed. The reaction was heated with stirring in a microwave at 160° C. for 75 minutes. The reaction was cooled before filtering through celite and concentrating in vacuo. The reaction mixture was purified by preparative column chromatography using acidic eluent to afford the named product (22.8 mg). LCMS $R_t$=3.62 min, m/z (ES+) 375 (M+H).

Example 2

{2-[5-(3,5-Dichloro-phenylamino)-2-fluoro-phenyl]-acetylamino}-acetic acid

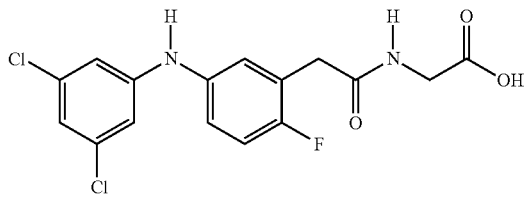 [SMILES: O=C(O)CNC(=O)Cc1cc(Nc2cc(Cl)cc(Cl)c2)ccc1F]

[2-(2-Fluoro-5-nitro-phenyl)-acetylamino]-acetic acid tert-butyl ester

To a stirred solution of 2-fluoro-5-nitrophenylacetic acid (1.00 g, 5.0 mmol) in DCM (40 ml) was added HATU (2.11 g, 7.5 mmol) in one portion and the reaction stirred for 5 minutes. Glycine t-butyl ester (1.03 ml, 7.5 mmol) and diisopropylethylamine (1.78 ml, 10 mmol) were added and the reaction stirred overnight. The reaction was washed with water, separated, the organic layer dried over sodium sulfate, filtered and concentrated onto silica in vacuo. The reaction was purified by column chromatography eluting with 100% EtOAc to afford the named product (1.57 g). LCMS $R_t$=3.48 min, m/z (ES+) 257 (MH-t-Butyl).

[2-(Fluoro-5-aminophenyl)-acetylamino]-acetic acid tert-butyl ester

To a stirred solution of [2-(fluoro-5-nitrophenyl)-acetylamino]-acetic acid tert-butyl ester (1.57 g, 5.0 mmol) in methanol (50 ml) under an atmosphere of nitrogen was added 10% Pd/C (50% wet) (10 Wt %, 300 mg) in one portion. The reaction was evacuated, placed under an atmosphere of hydrogen (1 bar) and stirred vigorously overnight. The reaction was filtered through celite and the filtrate concentrated in vacuo. The crude mixture was purified using an SCX solid phase extraction cartridge eluting with MeOH: 5% ammonium hydroxide to afford the named product (1.27 g). LCMS $R_t$=2.11 min, m/z (ES+) 283 (M+H).

{2-[5-(3,5-Dichlorophenylamino)-2-fluorophenyl]-acetylamino}-acetic acid tert-butyl ester To a stirred solution of [2-(fluoro-5-aminophenyl)-acetylamino]-acetic acid tert-butyl ester (0.160 g, 0.57 mmol), 3,5-dichloro-1-bromobenzene (0.156 g, 0.69 mmol), $K_2CO_3$ (0.147 g, 1.06 mmol) and xantphos (0.031 g, 0.057 mmol) in 1,4-dioxane (2 ml) under nitrogen in a microwave tube was added $Pd_2dba_3$ (0.024 g, 0.028 mmol) in one portion and the tube sealed. The reaction was heated with stirring in a microwave at 160° C. for 60 minutes. The reaction was cooled before filtering through celite and concentrating in vacuo. The reaction mixture was purified by column chromatography using 1:1 EtOAc:Hexane as eluent to afford the named product (145 mg). LCMS $R_t$=4.57 min, m/z (ES−) 425 (M−H).

To a stirred solution of {2-[5-(3,5-dichlorophenylamino)-2-fluorophenyl]-acetylamino}-acetic acid tert-butyl ester (145 mg, 0.34 mmol) in DCM (3 ml) was added trifluroacetic acid (0.30 ml) and the reaction stirred overnight. The reaction was concentrated in vacuo and purified by preparative chromatography to afford the named product (35 mg). LCMS $R_t$=3.86 min, m/z (ES+) 371 (M+H).

Example 3

2-[4-(2,6-Dichloro-4-trifluoromethyl-phenylamino)-phenyl]-N-(2-hydroxy-ethyl)-acetamide

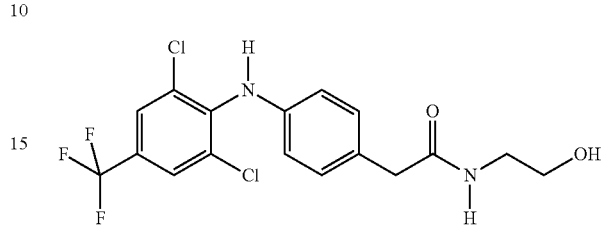

(4-Nitrophenyl)-acetic acid 2,5-dioxopyrrolidin-1-yl ester

To a stirred solution of 4-nitrophenyl acetic acid (1.00 g, 5.53 mmol) and dimethylformamide (catalytic, 3 drops) in dichloromethane (50 ml) was added oxalyl chloride (0.59 ml, 6.91 mmol) dropwise via syringe and the reaction stirred at room temperature for 30 minutes. N-hydroxysuccinamide (0.667 g, 5.80 mmol) and triethylamine (1.92 ml, 13.81 mmol) were added in one portion and the reaction left to stir at room temperature overnight. The reaction was washed with water, separated, the organic layer dried over sodium sulfate, filtered and concentrated onto silica in vacuo. The reaction was purified by column chromatography eluting with 5% MeOH:DCM to afford the named product (1.021 g). $R_f$ (2% MeOH:DCM) 0.08; LC $R_t$=3.44 min N-(2-Hydroxyethyl)-2-(4-nitrophenyl)-acetamide To a stirred solution of (4-nitrophenyl)-acetic acid 2,5-dioxopyrrolidin-1-yl ester (0.500 g, 1.80 mmol) in acetonitrile (10 ml) was added 2-aminoethanol (119 µL, 1.98 mmol) in one portion and the reaction left to stir at room temperature overnight. The reaction was filtered, concentrated onto silica in vacuo and purified by column chromatography eluting with 10% MeOH:DCM to afford the named product (0.237 g). $R_f$ (5% MeOH:DCM) 0.13; LCMS $R_t$=2.06 min, m/z (ES+) 225 (M+H).

2-(4-Aminophenyl)-N-(2-hydroxyethyl)-acetamide

To a stirred solution of N-(2-hydroxyethyl)-2-(4-nitrophenyl)acetamide (0.237 g, 1.06 mmol) in methanol (15 ml) under an atmosphere of nitrogen was added 10% Pd/C (10 Wt %, 24 mg) in one portion. The reaction was evacuated, placed under an atmosphere of hydrogen (1 bar) and stirred vigorously overnight. The reaction was filtered through celite and the filtrate concentrated in vacuo. The crude mixture was purified using an SCX solid phase extraction cartridge eluting with 10% MeOH:DCM to afford the named product (0.130 g). LCMS $R_t$=0.98 min, m/z (ES+) 195 (M+H).

N-(2-Hydroxyethyl)-2-[4-(2,4,6-trichlorophenylamino)phenyl]-acetamide

To a stirred solution of 2-(4-aminophenyl)-N-(2-hydroxyethyl)-acetamide (0.100 g, 0.52 mmol), 2,6-dichloro-4-trifluromethylbromobenzene (0.189 g, 0.65 mmol), $K_2CO_3$ (0.178 g, 1.30 mmol) and xantphos (0.030 g, 0.052 mmol) in 1,4-dioxane (2 ml) under nitrogen in a microwave tube was added $Pd_2dba_3$ (0.024 g, 0.026 mmol) in one portion and the tube sealed. The reaction was heated with stirring in a microwave at 160° C. for 75 minutes. The reaction was cooled before filtering through celite and concentrating in vacuo. The reaction mixture was purified by preparative column chromatography using acidic eluent to afford the named product (38.2 mg). LCMS $R_t$=3.75 min, m/z (ES+) 407 (M+H).

Example 4

{2-[4-(3,5-Dichlorophenylamino)-phenyl]-acetylamino}-acetic acid

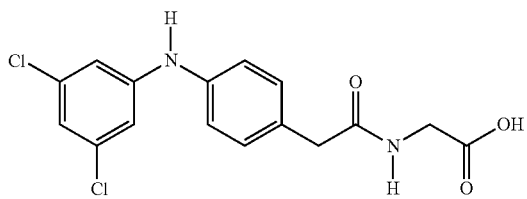 [SMILES: O=C(O)CNC(=O)Cc1ccc(Nc2cc(Cl)cc(Cl)c2)cc1]

[2-(4-Nitrophenyl)-acetylamino]-acetic acid tert-butyl ester

To a stirred solution of 4-nitrophenyl acetic acid (1.00 g, 5.53 mmol) and dimethylformamide (catalytic, 3 drops) in dichloromethane (25 ml) was added oxalyl chloride (0.59 ml, 6.91 mmol) dropwise via syringe and the reaction stirred at room temperature for 30 minutes. Glycine tert-butyl ester (1.44 g, 11.06 mmol) was added in one portion and the reaction left to stir at room temperature for 1 hour. The reaction was washed with water, separated, the organic layer dried over sodium sulfate, filtered and concentrated onto silica in vacuo. The reaction was purified by column chromatography eluting with 1:1 EtOAc:Hexane as eluent to afford the named product (0.900 g). LCMS $R_t$=3.30 min, m/z (ES+) 295 (M+H).

[2-(4-Aminophenyl)-acetylamino]-acetic acid tert-butyl ester

To a stirred solution of [2-(4-nitrophenyl)-acetylamino]-acetic acid tert-butyl ester (1.10 g, 4.17 mmol) in methanol (20 ml) under an atmosphere of nitrogen was added 10% Pd/C (50% wet) (7 Wt %, 150 mg) in one portion. The reaction was evacuated, placed under an atmosphere of hydrogen (1 bar) and stirred vigorously overnight. The reaction was filtered through celite and the filtrate concentrated in vacuo to afford the named product (0.900 g,). LCMS $R_t$=2.57 min, m/z (ES+) 265 (M+H).

{2-[4-(3,5-Dichlorophenylamino)-phenyl]-acetylamino}acetic acid

To a stirred solution of [2-(4-aminophenyl)-acetylamino]-acetic acid tert-butyl ester (0.200 g, 0.76 mmol), 3,5-dichloro-1-bromobenzene (0.186 g, 0.83 mmol), $K_2CO_3$ (0.524 g, 3.80 mmol) and xantphos (0.050 g, 0.087 mmol) in 1,4-dioxane (2 ml) under nitrogen in a microwave tube was added $Pd_2dba_3$ (0.050 g, 0.054 mmol) in one portion and the tube sealed. The reaction was heated with stirring in a microwave at 160° C. for 75 minutes. The reaction was cooled before filtering through celite and concentrating in vacuo. The reaction mixture was purified by preparative column chromatography using acidic eluent. The purified tert-butyl ester product was dissolved in 3:1 DCM:trifluoroacetic acid (4 ml) and the reaction stirred at room temperature overnight. The reaction was concentrated in vacuo and the crude product purified by preparative chromatography to afford the named product (10.6 mg). LCMS $R_t$=3.76 min, m/z (ES+) 353 (M+H).

Using the General Methods Described Above the Following Compounds were Also Prepared:

| Example | Structure | Name | m/z (ES+, M + H) |
|---|---|---|---|
| 5 | 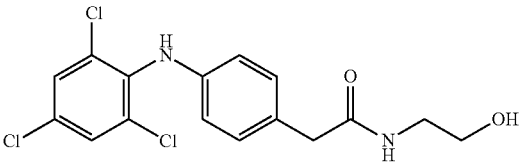 [SMILES: O=C(Cc1ccc(Nc2c(Cl)cc(Cl)cc2Cl)cc1)NCCO] | N-(2-Hydroxy-ethyl)-2-[4-(2,4,6-trichloro-phenylamino)-phenyl]acetamide | 375 |
| 6 | 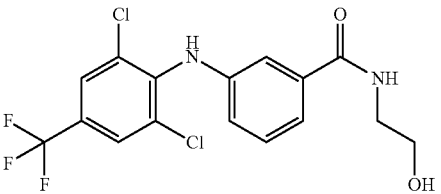 [SMILES: O=C(NCCO)c1cccc(Nc2c(Cl)cc(C(F)(F)F)cc2Cl)c1] | 3-(2,6-Dichloro-4-trifluoromethyl-phenylamino)-N-(2-hydroxy-ethyl)benzamide | 395 |

-continued

| Example | Structure | Name | m/z (ES+, M + H) |
|---|---|---|---|
| 7 | 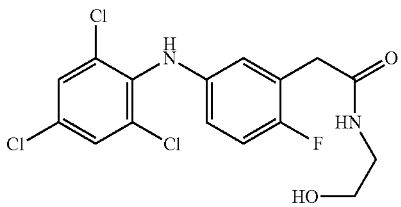 [SMILES: O=C(Cc1cc(Nc2c(Cl)cc(Cl)cc2Cl)ccc1F)NCCO] | 2-[2-Fluoro-5-(2,4,6-trichloro-phenylamino)-phenyl]-N-(2-hydroxy-ethyl)-acetamide | 393 |
| 8 | 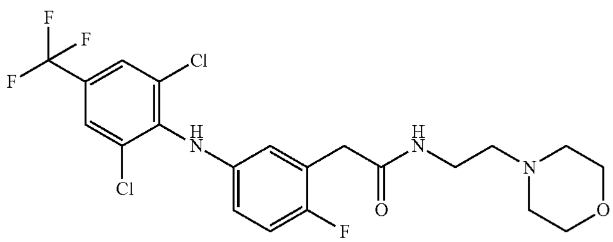 [SMILES: O=C(Cc1cc(Nc2c(Cl)cc(C(F)(F)F)cc2Cl)ccc1F)NCCN1CCOCC1] | 2-[5-(2,6-Dichloro-4-trifluoromethyl-phenylamino)-2-fluoro-phenyl]-N-(2-morpholin-4-yl-ethyl)-acetamide | 494 |
| 9 | 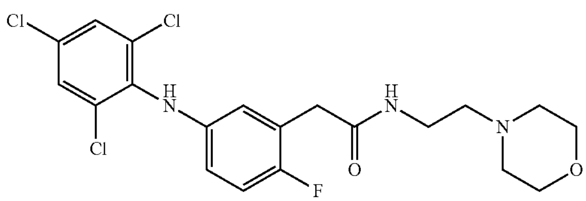 [SMILES: O=C(Cc1cc(Nc2c(Cl)cc(Cl)cc2Cl)ccc1F)NCCN1CCOCC1] | 2-[2-Fluoro-5-(2,4,6-trichloro-phenylamino)-phenyl]-N-(2-morpholin-4-yl-ethyl)-acetamide | 462 |
| 10 | 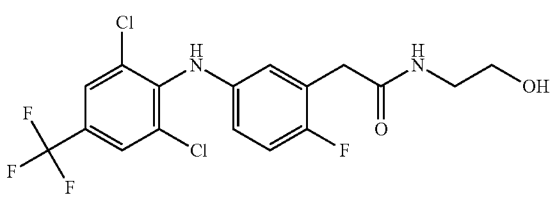 [SMILES: O=C(Cc1cc(Nc2c(Cl)cc(C(F)(F)F)cc2Cl)ccc1F)NCCO] | 2-[5-(2,6-Dichloro-4-trifluoromethyl-phenylamino)-2-fluoro-phenyl]-N-(2-hydroxy-ethyl)-acetamide | 425 |
| 11 | 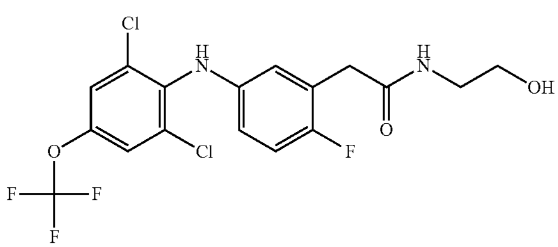 [SMILES: O=C(Cc1cc(Nc2c(Cl)cc(OC(F)(F)F)cc2Cl)ccc1F)NCCO] | 2-[5-(2,6-Dichloro-4-trifluoromethoxy-phenylamino)-2-fluoro-phenyl]-N-(2-hydroxy-ethyl)-acetamide | 441 |
| 12 | 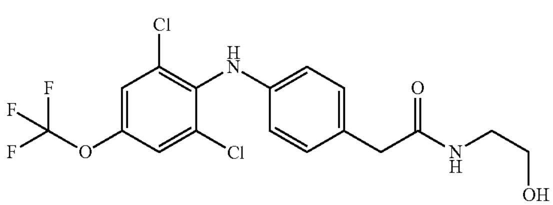 [SMILES: O=C(Cc1ccc(Nc2c(Cl)cc(OC(F)(F)F)cc2Cl)cc1)NCCO] | 2-[4-(2,6-Dichloro-4-trifluoromethoxy-phenylamino)-phenyl]-N-(2-hydroxy-ethyl)-acetamide | 423 |
| 13 | 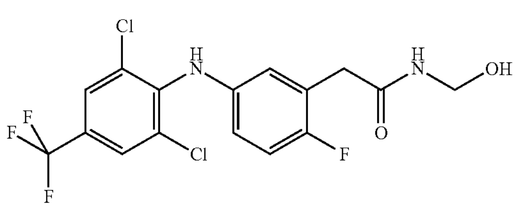 [SMILES: O=C(Cc1cc(Nc2c(Cl)cc(C(F)(F)F)cc2Cl)ccc1F)NCO] | 5-(2,6-Dichloro-4-trifluoromethyl-phenylamino)-2-fluoro-N-(2-hydroxy-ethyl)-benzamide | 413 |

-continued

| Example | Structure | Name | m/z (ES+, M + H) |
|---|---|---|---|
| 14 | 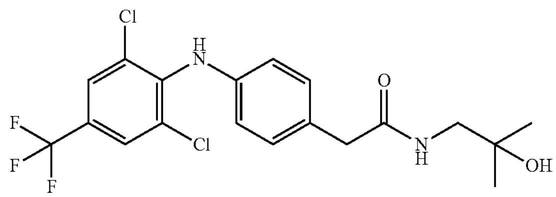 [SMILES: CC(C)(O)CNC(=O)Cc1ccc(Nc2c(Cl)cc(C(F)(F)F)cc2Cl)cc1] | 2-[4-(2,6-Dichloro-4-trifluoromethyl-phenylamino)-phenyl]-N-(2-hydroxy-2-methyl-propyl)-acetamide | 435 |
| 15 | 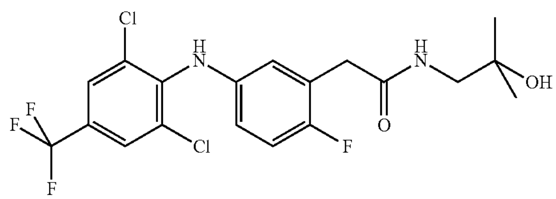 [SMILES: CC(C)(O)CNC(=O)Cc1cc(Nc2c(Cl)cc(C(F)(F)F)cc2Cl)ccc1F] | 2-[5-(2,6-Dichloro-4-trifluoromethyl-phenylamino)-2-fluoro-phenyl]-N-(2-hydroxy-2-methyl-propyl)-acetamide | 455 |
| 16 | 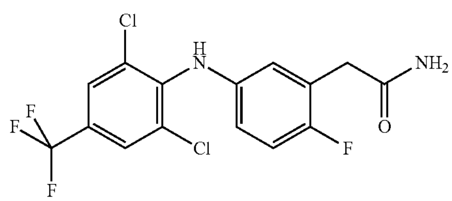 [SMILES: NC(=O)Cc1cc(Nc2c(Cl)cc(C(F)(F)F)cc2Cl)ccc1F] | 2-[5-(2,6-Dichloro-4-trifluoromethyl-phenylamino)-2-fluoro-phenyl]-acetamide | 382 |
| 17 | 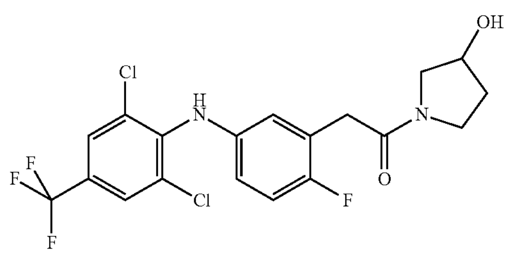 [SMILES: O=C(Cc1cc(Nc2c(Cl)cc(C(F)(F)F)cc2Cl)ccc1F)N1CCC(O)C1] | 2-[5-(2,6-Dichloro-4-trifluoromethyl-phenylamino)-2-fluoro-phenyl]-1-(3-hydroxy-pyrrolidin-1-yl)-ethanone | 452 |
| 18 | 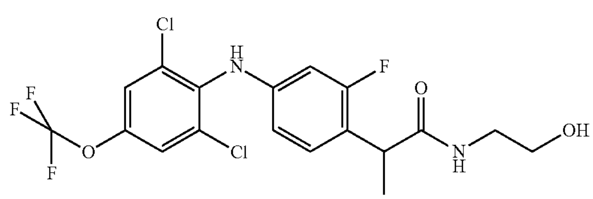 [SMILES: CC(C(=O)NCCO)c1ccc(Nc2c(Cl)cc(OC(F)(F)F)cc2Cl)cc1F] | 2-[4-(2,6-Dichloro-4-trifluoromethoxy-phenylamino)-2-fluoro-phenyl]-N-(2-hydroxy-ethyl)-propionamide | 455 |
| 19 | 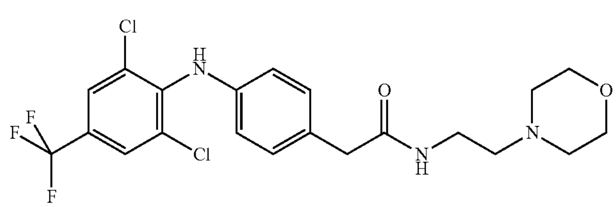 [SMILES: O=C(Cc1ccc(Nc2c(Cl)cc(C(F)(F)F)cc2Cl)cc1)NCCN1CCOCC1] | 2-[4-(2,6-Dichloro-4-trifluoromethyl-phenylamino)-phenyl]-N-(2-morpholin-4-yl-ethyl)-acetamide | 478 |
| 20 | 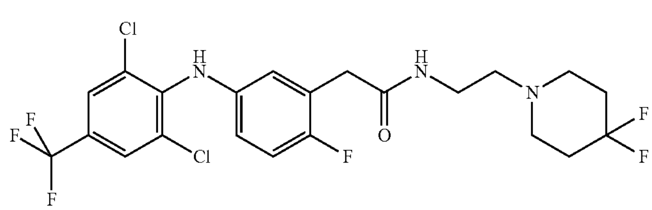 [SMILES: O=C(Cc1cc(Nc2c(Cl)cc(C(F)(F)F)cc2Cl)ccc1F)NCCN1CCC(F)(F)CC1] | 2-[5-(2,6-Dichloro-4-trifluoromethyl-phenylamino)-2-fluoro-phenyl]-N-[2-(4,4-difluoro-piperidin-1-yl)-ethyl]-acetamide | 529 |

| Example | Structure | Name | m/z (ES+, M + H) |
|---|---|---|---|
| 21 | 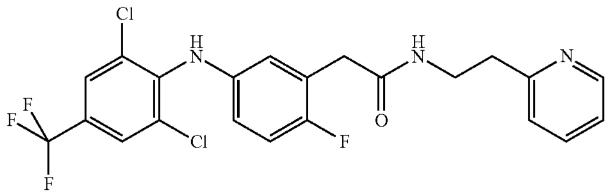 [SMILES: O=C(Cc1cc(Nc2c(Cl)cc(C(F)(F)F)cc2Cl)ccc1F)NCCc1ccccn1] | 2-[5-(2,6-Dichloro-4-trifluoromethyl-phenylamino)-2-fluoro-phenyl]-N-(2-pyridin-2-yl-ethyl)-acetamide | 487 |
| 22 | 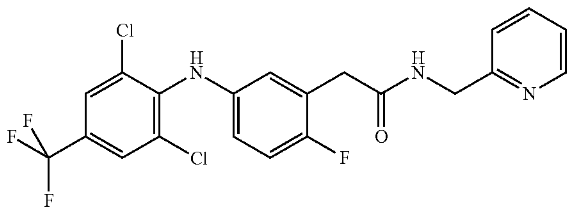 [SMILES: O=C(Cc1cc(Nc2c(Cl)cc(C(F)(F)F)cc2Cl)ccc1F)NCc1ccccn1] | 2-[5-(2,6-Dichloro-4-trifluoromethyl-phenylamino)-2-fluoro-phenyl]-N-pyridin-2-ylmethyl-acetamide | 473 |

Test Examples

Summary

The objective of this study was to examine the in vitro effects of the Example compounds on the KCNQ2/KCNQ3 potassium channel current expressed in mammalian cells using the PatchXpress 7000A (Molecular Devices), an automatic parallel patch clamp system. The test compounds were evaluated at 30 μM with this concentration tested in 3 cells (n=3). The duration of exposure to the test compound concentration was 5 minutes. The compounds were found to produce a concentration-dependent enhancement of the current. Table 1 shows the individual results for the compounds. The results for a positive control, flupirtine (Table 2) confirm the sensitivity of the test system to detect KCNQ2/KCNQ3 current enhancement.

Methods

Cell Treatments

All experiments were performed at ambient temperature. Each cell acted as its own control.

Test Article Treatment Groups

A 30 μM concentration of test compound was applied via disposable polyethylene micropipette tips to naïve cells (n=2, where n=the number cells). Each solution exchange, performed in quadruplicate, consisted of aspiration and replacement of 45 μL of the total 50 μL volume of the extracellular well of the Sealchip$_{16}$.

Positive Control Treatment Groups

Vehicle was applied to naïve cells (n≥2, where n=the number cells), for a 5 minute exposure interval. Each solution exchange, performed in quadruplicate, consisted of aspiration and replacement of 45 μL of the total 50 μL volume of the extracellular well of the Sealchip$_{16}$. After vehicle application, the positive control was applied in the same manner, to verify sensitivity of the assay.

Automated Patch Clamp Procedures

In preparation for a recording session, intracellular solution was loaded into the intracellular compartments of the Sealchip$_{16}$ planar electrode. Cell suspension was pipetted into the extracellular compartments of the Sealchip$_{16}$ planar electrode. After establishment of a whole-cell configuration, membrane currents were recorded using dual-channel patch clamp amplifiers in the PatchXpress® system. Before digitization, the current records were low-pass filtered at one-fifth of the sampling frequency.

Data Analysis

Data acquisition and analyses were performed using the suite of pCLAMP programs (Axon Instruments, Union City, Calif.). Steady state was defined by the limiting constant rate of change with time (linear time dependence). The steady state before and after test article application was used to calculate the percentage of current inhibited at each concentration. Results obtained from different cell were averaged and presented as Mean±S.D.—see Tables 1 and 2.

TABLE 1

| Test Article ID | Conc. (μM) | n | Mean % Enhancement of KCNQ2/KCNQ3 |
|---|---|---|---|
| Example 1 | 30 | 3 | 168.2 |
| Example 2 | 30 | 3 | 162.5 |
| Example 3 | 30 | 3 | 115.8 |
| Example 4 | 30 | 3 | 181.9 |

Positive Control

TABLE 2

| Test Article ID | Conc. (μM) | n | Mean % Enhancement of KCNQ2/KCNQ3 |
|---|---|---|---|
| Flupirtine | 10 | 6 | 201.0 |

It can be seen from the results in Table 1 that the example compounds of the present application showed excellent enhancement of the KCNQ2/KCNQ3 potassium channel current.

What is claimed is:

1. A method of enhancing KCNQ2/KCNQ3 voltage-dependent potassium channels, wherein diseases treatable by such enhancement are selected from the group consisting of Lower Urinary Tract Disorders, Gynaecological Pain, Cardiac Arrhythmias, Thromboembolic Events, Cardiovascular Diseases, Gastrointestinal Disorders and Visceral Smooth Muscle Disorders, the method comprising administering to a patient in need thereof an effective amount of a compound of formula (I):

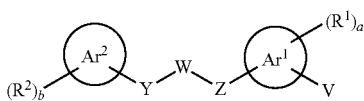

(I)

or a pharmaceutically acceptable salt thereof,
wherein:
$Ar^1$ and $Ar^2$ are each phenyl;
a is 1;
$R^1$ is halogen;
b is an integer of from 0 to 3;
$R^2$ is selected from the group consisting of alkyl having from 1 to 3 carbon atoms, halogen, haloalkyl having from 1 to 3 carbon atoms, alkoxy having from 1 to 3 carbon atoms, haloalkoxy having from 1 to 3 carbon atoms, carboxyl, amino, hydroxyl and cyano, and where b is greater than 1, each substituent $R^2$ may be the same or different;
V is $(CR^{3a}R^{3b})_p CON(R^{3b})X$, wherein said group is in the 3-(meta) or 4-(para) position with respect to the substituent Z;
W is $NR^{4a}$, wherein $R^{4a}$ is selected from the group consisting of hydrogen, alkyl having from 1 to 3 carbon atoms and phenyl;
X is a substituent selected from the group consisting of hydroxyalkyl having from 1 to 4 carbon atoms, polyalkylene glycol residue of general formula:

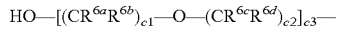

$HO-[(CR^{6a}R^{6b})_{c1}-O-(CR^{6c}R^{6d})_{c2}]_{c3}-$ wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different and each is a hydrogen or an alkyl having from 1 to 4 carbon atoms, alkoxyalkyl comprising an alkyl having from 1 to 4 carbon atoms that is substituted with at least one alkoxy having from 1 to 4 carbon atoms, carboxyalkyl comprising an alkyl having from 1 to 4 carbon atoms that is substituted with at least one carboxy, carboxyalkyl comprising alkyl having from 1 to 4 carbon atoms which are substituted with at least one carboxy and alkoxycarbonylalkyl comprising alkyl having from 1 to 4 carbon atoms which are substituted with at least one alkoxycarbonyl having from 2 to 5 carbon atoms;
Y and Z are each a group of formula $(CR^{5a}R^{5b})_{n1}$ wherein each n1 is 0;

$R^{3a}$ and $R^{3b}$ are the same or different and each is selected from the group consisting of hydrogen and alkyl; and
p is an integer of from 0 to 2.

2. The method according to claim 1, wherein V is $(CR^{3a}R^{3b})_p CON(R^{3b})X$, wherein said groups is in the 3-(meta) or 4-(para) position with respect to the substituent Z, wherein p is an integer of 0 or 1, each of $R^{3a}$ and $R^{3b}$ is hydrogen, and X is selected from the group consisting of alkyl having 1 or 2 carbon atoms which are substituted with a group selected from hydroxyl groups, methoxy groups, ethoxy groups, carboxy groups, methoxycarbonyl groups and ethoxycarbonyl groups.

3. A compound according to claim 1 or a pharmacologically acceptable salt or prodrug thereof, selected from the group consisting of:
{2-[5-(3,5-dichlorophenylamino)-2-fluorophenyl]-acetylamino}acetic acid;
2-[5-(2,6-dichloro-4-trifluoromethoxy-phenylamino)-2-fluoro-phenyl]-N-(2-hydroxy-ethyl)acetamide;
5-(2,6-dichloro-4-trifluoromethyl-phenylamino)-2-fluoro-N-(2-hydroxy-ethyl)-benzamide;
2-[5-(2,6-dichloro-4-trifluoromethyl-phenylamino)-2-fluoro-phenyl]-N-(2-hydroxy-2-methyl-propyl)acetamide; and
2-[4-(2,6-dichloro-4-trifluoromethoxy-phenylamino)-2-fluoro-phenyl]-N-(2-hydroxy-ethyl)propionamide.

4. The method according to claim 1, wherein said compound forms a part of a pharmaceutical composition which further comprises a pharmacologically acceptable diluent or carrier.

5. The method according to claim 4, wherein said pharmaceutical composition further comprises at least one compound selected from the group consisting of muscarinic receptor antagonists, β3 adrenergic receptor agonists, neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), 5-HT antagonists, alpha-1 adrenoceptor antagonists, tricyclic anti-depressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs).

* * * * *